US012805799B2

(12) United States Patent
Ousdigian et al.

(10) Patent No.: US 12,805,799 B2
(45) Date of Patent: Nov. 24, 2026

(54) PREDICTION OF VENTRICULAR TACHYCARDIA OR VENTRICULAR FIBRILLATION TERMINATION TO LIMIT THERAPIES AND EMERGENCY MEDICAL SERVICE OR BYSTANDER ALERTS

(71) Applicant: Medtronic, Inc., Minneapolis, MN (US)

(72) Inventors: Kevin T. Ousdigian, Shoreview, MN (US); Jeffrey M. Gillberg, Minneapolis, MN (US); Shantanu Sarkar, Roseville, MN (US); Sean R. Landman, Minneapolis, MN (US); Abhijit Kadrolkar, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 70 days.

(21) Appl. No.: 18/832,033

(22) PCT Filed: Feb. 9, 2023

(86) PCT No.: PCT/US2023/062304
§ 371 (c)(1),
(2) Date: Jul. 22, 2024

(87) PCT Pub. No.: WO2023/154809
PCT Pub. Date: Aug. 17, 2023

(65) Prior Publication Data

US 2025/0090090 A1 Mar. 20, 2025

Related U.S. Application Data

(60) Provisional application No. 63/267,823, filed on Feb. 10, 2022.

(51) Int. Cl.
*A61B 5/00* (2006.01)
*A61B 5/361* (2021.01)
(Continued)

(52) U.S. Cl.
CPC ............ *A61B 5/4836* (2013.01); *A61B 5/361* (2021.01); *A61B 5/363* (2021.01); *A61B 5/686* (2013.01);
(Continued)

(58) Field of Classification Search
CPC ....... A61B 5/4836; A61B 5/361; A61B 5/363; A61B 5/686; A61B 5/7267; A61B 5/7275;
(Continued)

(56) References Cited

U.S. PATENT DOCUMENTS

| | | |
|---|---|---|
| 3,552,386 A | 1/1971 | Horth |
| 3,598,110 A | 8/1971 | Edmark |

(Continued)

FOREIGN PATENT DOCUMENTS

| | | |
|---|---|---|
| CA | 3075015 A1 | 9/2021 |
| CN | 105769171 A | 7/2016 |

(Continued)

OTHER PUBLICATIONS

International Preliminary Report on Patentability from International Application No. PCT/US2023/062304 dated Aug. 22, 2024, 7 pp.

(Continued)

*Primary Examiner* — Michael Tomaszewski
(74) *Attorney, Agent, or Firm* — Shumaker & Sieffert, P.A.

(57) ABSTRACT

Devices, systems, and techniques are disclosed for determining the likelihood that a cardiac event will self-terminate. An example technique includes determining, by processing circuitry and based on current sensed physiological parameters of a patient, that a cardiac event is occurring in the patient. The example technique includes determining, by the processing circuitry- and based on the current sensed physiological parameters of the patient, that the cardiac (Continued)

event is unlikely to self-terminate within a predetermined period of time. The example technique includes, in response to determining that the cardiac event is unlikely- to self-terminate, deliver therapy to the patient or issue an alert.

18 Claims, 12 Drawing Sheets

(51) Int. Cl.

| | |
|---|---|
| ***A61B 5/363*** | (2021.01) |
| ***A61N 1/362*** | (2006.01) |
| ***A61N 1/365*** | (2006.01) |
| ***A61N 1/37*** | (2006.01) |
| ***G16H 10/60*** | (2018.01) |
| ***G16H 20/40*** | (2018.01) |
| ***G16H 50/30*** | (2018.01) |

(52) U.S. Cl.
CPC .......... *A61B 5/7267* (2013.01); *A61B 5/7275* (2013.01); *A61B 5/7282* (2013.01); *A61B 5/746* (2013.01); *A61N 1/3621* (2013.01); *A61N 1/365* (2013.01); *A61N 1/3702* (2013.01); *G16H 10/60* (2018.01); *G16H 20/40* (2018.01); *G16H 50/30* (2018.01)

(58) Field of Classification Search
CPC ...... A61B 5/7282; A61B 5/746; G16H 20/40; G16H 10/60; G16H 50/30; A61N 1/3621; A61N 1/365; A61N 1/3702
USPC .......................................................... 600/301
See application file for complete search history.

(56) References Cited

U.S. PATENT DOCUMENTS

| | | | | |
|---|---|---|---|---|
| 3,658,055 | A | | 4/1972 | Abe et al. |
| 3,677,260 | A | | 7/1972 | Funfstuck et al. |
| 3,828,768 | A | | 8/1974 | Douglas |
| 3,861,387 | A | | 1/1975 | Lawhom et al. |
| 3,927,663 | A | | 12/1975 | Russell et al. |
| 4,023,564 | A | | 5/1977 | Valiquette et al. |
| 4,306,567 | A | | 12/1981 | Krasner |
| 4,457,315 | A | | 7/1984 | Bennish |
| 4,958,641 | A | | 9/1990 | Digby et al. |
| 5,065,766 | A | | 11/1991 | Sasaki |
| 5,217,021 | A | | 6/1993 | Steinhaus et al. |
| 5,271,411 | A | | 12/1993 | Ripley et al. |
| 5,366,487 | A | | 11/1994 | Adams et al. |
| 5,370,667 | A | * | 12/1994 | Alt .................... A61N 1/39622 607/19 |
| 5,404,877 | A | | 4/1995 | Nolan et al. |
| 5,416,695 | A | | 5/1995 | Stutman et al. |
| 5,458,123 | A | | 10/1995 | Unger |
| 6,095,984 | A | | 8/2000 | Amana et al. |
| 6,129,678 | A | | 10/2000 | Ryan et al. |
| 6,292,687 | B1 | | 9/2001 | Lowell et al. |
| 6,485,429 | B2 | | 11/2002 | Forstner |
| 6,487,442 | B1 | | 11/2002 | Wood |
| 6,490,478 | B1 | | 12/2002 | Zhang et al. |
| 6,493,581 | B2 | | 12/2002 | Russell |
| 6,609,023 | B1 | | 8/2003 | Fischell et al. |
| 6,907,238 | B2 | | 6/2005 | Leung |
| 6,980,112 | B2 | | 12/2005 | Nee |
| 7,076,290 | B2 | | 7/2006 | Sheth et al. |
| 7,092,751 | B2 | | 8/2006 | Erkkila |
| 7,117,031 | B2 | | 10/2006 | Lohman et al. |
| 7,194,354 | B1 | | 3/2007 | Oran et al. |
| 7,212,849 | B2 | | 5/2007 | Zhang et al. |
| 7,312,709 | B2 | | 12/2007 | Kingston |
| 7,343,199 | B2 | | 3/2008 | Hatlestad et al. |
| 7,353,179 | B2 | | 4/2008 | Ott et al. |
| 7,396,330 | B2 | | 7/2008 | Banet et al. |
| 7,480,529 | B2 | | 1/2009 | Li |
| 7,558,623 | B2 | | 7/2009 | Fischell et al. |
| 7,689,282 | B2 | | 3/2010 | Zhang et al. |
| 7,702,382 | B2 | | 4/2010 | Xue |
| 7,715,905 | B2 | | 5/2010 | Kurzweil et al. |
| 7,733,224 | B2 | | 6/2010 | Tran |
| 7,801,596 | B2 | | 9/2010 | Fischell et al. |
| 7,840,277 | B2 | | 11/2010 | Matos |
| 7,844,323 | B2 | | 11/2010 | Fischell et al. |
| 7,846,106 | B2 | | 12/2010 | Andrews et al. |
| 7,860,559 | B2 | | 12/2010 | Fischell et al. |
| 7,889,092 | B2 | | 2/2011 | Volk et al. |
| 7,894,883 | B2 | | 2/2011 | Gunderson et al. |
| 7,991,460 | B2 | | 8/2011 | Fischell et al. |
| 8,073,536 | B2 | | 12/2011 | Gunderson et al. |
| 8,073,537 | B2 | | 12/2011 | Gunderson et al. |
| 8,170,653 | B2 | | 5/2012 | Fischell et al. |
| 8,204,580 | B2 | | 6/2012 | Kurzweil et al. |
| 8,214,043 | B2 | | 7/2012 | Matos |
| 8,224,430 | B2 | | 7/2012 | Fischell et al. |
| 8,239,020 | B2 | | 8/2012 | Zhang et al. |
| 8,265,740 | B2 | | 9/2012 | Fischell et al. |
| 8,265,751 | B2 | | 9/2012 | Zhang et al. |
| 8,301,232 | B2 | | 10/2012 | Albert et al. |
| 8,301,236 | B2 | | 10/2012 | Baumann et al. |
| 8,332,233 | B2 | | 12/2012 | Ott et al. |
| 8,352,018 | B2 | | 1/2013 | Xue |
| 8,369,936 | B2 | | 2/2013 | Farringdon et al. |
| 8,401,644 | B2 | | 3/2013 | Gunderson et al. |
| 8,423,128 | B2 | | 4/2013 | Goto |
| 8,433,399 | B1 | | 4/2013 | Nosrati et al. |
| 8,437,840 | B2 | | 5/2013 | Patel et al. |
| 8,461,988 | B2 | | 6/2013 | Tran |
| 8,473,065 | B2 | | 6/2013 | Matos |
| 8,483,807 | B2 | | 7/2013 | Kurzweil et al. |
| 8,512,257 | B2 | | 8/2013 | Fischell et al. |
| 8,521,281 | B2 | | 8/2013 | Patel et al. |
| 8,525,673 | B2 | | 9/2013 | Tran |
| 8,525,687 | B2 | | 9/2013 | Tran |
| 8,531,291 | B2 | | 9/2013 | Tran |
| 8,554,315 | B2 | | 10/2013 | Cho et al. |
| 8,560,069 | B2 | | 10/2013 | Zhang |
| 8,565,882 | B2 | | 10/2013 | Matos |
| 8,583,251 | B2 | | 11/2013 | Matos |
| 8,630,702 | B2 | | 1/2014 | Fischell et al. |
| 8,680,991 | B2 | | 3/2014 | Tran |
| 8,682,284 | B2 | | 3/2014 | Brackett et al. |
| 8,706,225 | B2 | | 4/2014 | Matos |
| 8,718,752 | B2 | | 5/2014 | Libbus et al. |
| 8,738,120 | B2 | | 5/2014 | Björling et al. |
| 8,747,336 | B2 | | 6/2014 | Tran |
| 8,774,908 | B2 | | 7/2014 | Stewart |
| 8,774,909 | B2 | | 7/2014 | Patel et al. |
| 8,805,529 | B2 | | 8/2014 | Matos |
| 8,825,146 | B2 | | 9/2014 | Li |
| 8,831,725 | B2 | | 9/2014 | Gunderson et al. |
| 8,849,400 | B2 | | 9/2014 | Gunderson et al. |
| 8,862,393 | B2 | | 10/2014 | Zhou et al. |
| 8,886,296 | B2 | | 11/2014 | Patel et al. |
| 8,909,332 | B2 | | 12/2014 | Vitali et al. |
| 8,923,960 | B2 | | 12/2014 | Goto |
| 8,954,137 | B2 | | 2/2015 | Kurzweil et al. |
| 8,965,494 | B2 | | 2/2015 | Fischell et al. |
| 8,983,587 | B2 | | 3/2015 | Kurzweil et al. |
| 9,031,645 | B2 | | 5/2015 | Houben et al. |
| 9,044,148 | B2 | | 6/2015 | Michaelson et al. |
| 9,060,746 | B2 | | 6/2015 | Weng et al. |
| 9,082,156 | B2 | | 7/2015 | Matos |
| 9,095,727 | B2 | | 8/2015 | Matos |
| 9,101,278 | B2 | | 8/2015 | Fischell et al. |
| 9,113,830 | B2 | | 8/2015 | Galen et al. |
| 9,138,590 | B2 | | 9/2015 | Zhang et al. |
| 9,179,255 | B2 | | 11/2015 | Stephens et al. |
| 9,179,851 | B2 | | 11/2015 | Baumann et al. |
| 9,204,796 | B2 | | 12/2015 | Tran |
| 9,237,243 | B2 | | 1/2016 | Jensen et al. |
| 9,241,677 | B2 | | 1/2016 | Liao-Chen et al. |
| 9,293,025 | B2 | | 3/2016 | Zhang |
| 9,314,181 | B2 | | 4/2016 | Brockway et al. |

(56) References Cited

U.S. PATENT DOCUMENTS 9,351,640 B2 5/2016 Tran
9,364,158 B2 6/2016 Banet et al.
9,445,736 B2 9/2016 Kurzweil et al.
9,468,383 B2 10/2016 Fischell et al.
9,491,277 B2 11/2016 Vincent
9,498,152 B2 11/2016 Bowers
9,642,167 B1 5/2017 Snyder et al.
9,668,665 B2 6/2017 Schroeder et al.
9,681,814 B2 6/2017 Galloway et al.
9,724,008 B2 8/2017 Sullivan et al.
9,724,046 B2 8/2017 Forstner
9,730,604 B2 8/2017 Li et al.
9,735,896 B2 8/2017 Flippo et al.
9,770,181 B2 9/2017 Kurzweil et al.
9,775,520 B2 10/2017 Tran
9,820,667 B2 11/2017 Ting et al.
9,826,358 B2 11/2017 Ryan et al.
9,855,434 B2 1/2018 Matos
9,901,252 B2 2/2018 Tran
9,997,055 B2 6/2018 Ball
10,039,469 B2 8/2018 Higgins et al.
10,085,115 B2 9/2018 Mayor et al.
10,098,561 B2 10/2018 Brockway et al.
10,117,595 B2 11/2018 Chang et al.
10,123,741 B2 11/2018 Wang et al.
10,136,826 B2 11/2018 Sullivan et al.
10,159,415 B2 12/2018 Gopalakrishnan et al.
10,165,400 B2 12/2018 Rai
10,206,593 B2 2/2019 Ukil et al.
10,278,050 B2 4/2019 Winkler et al.
10,278,607 B2 5/2019 Prystowsky et al.
10,307,060 B2 6/2019 Tran
10,362,940 B2 7/2019 Tran
10,420,529 B2 9/2019 Wang et al.
10,463,295 B2 11/2019 Zhou
10,517,479 B2 12/2019 Tran
10,524,736 B2 1/2020 Gross
10,531,266 B2 1/2020 Rauner et al.
10,537,250 B2 1/2020 Albert
10,537,263 B2 1/2020 Català
10,540,878 B2 1/2020 Hunter et al.
10,575,748 B2 3/2020 Higgins et al.
10,595,731 B2 3/2020 Gopalakrishnan et al.
10,602,942 B2 3/2020 Shakur et al.
10,616,664 B2 4/2020 Alman et al.
10,616,747 B2 4/2020 Piett et al.
10,617,356 B2 4/2020 Wang et al.
10,657,796 B2 5/2020 Bowers
10,674,342 B2 6/2020 Park et al.
10,736,532 B2 8/2020 Bardy et al.
10,758,140 B2 9/2020 Kurzweil et al.
10,796,552 B2 10/2020 Fahey
10,888,705 B2 1/2021 Matos
10,905,328 B2 2/2021 Murphy et al.
10,967,187 B2 * 4/2021 Pei ........................ A61B 5/346
11,024,432 B2 6/2021 Chiu et al.
11,064,339 B2 7/2021 Hamre et al.
11,103,176 B2 8/2021 Galloway et al.
11,103,194 B2 8/2021 Galloway et al.
11,116,989 B2 9/2021 Gill et al.
11,160,484 B2 11/2021 Sullivan et al.
11,197,629 B2 12/2021 Remes et al.
11,198,017 B2 12/2021 Kaib et al.
11,202,174 B2 12/2021 Klinkner et al.
11,218,584 B2 1/2022 Martin et al.
11,219,373 B2 1/2022 Eggers et al.
11,228,891 B2 1/2022 King-Berkman et al.
11,230,242 B2 1/2022 Makled et al.
11,234,604 B2 2/2022 Albert
11,276,491 B2 3/2022 Petterson et al.
11,278,201 B2 3/2022 Thomson et al.
11,289,197 B1 3/2022 Park et al.
11,291,401 B2 4/2022 Velo
11,311,230 B2 4/2022 Sullivan et al.
11,341,839 B2 5/2022 Cruver et al.
11,344,244 B2 5/2022 Albert
11,363,952 B2 6/2022 Venkatraman et al.
11,406,314 B2 8/2022 Henry et al.
2003/0023175 A1 1/2003 Arzbaecher et al.
2003/0176798 A1 9/2003 Simon
2003/0191402 A1 10/2003 Arzbaecher et al.
2003/0204209 A1 * 10/2003 Burnes ............... A61N 1/39622
607/14
2004/0064062 A1 * 4/2004 Zhou ...................... A61B 5/364
600/515
2004/0172069 A1 9/2004 Hakala
2005/0065445 A1 3/2005 Arzbaecher et al.
2005/0154325 A1 7/2005 Lauter et al.
2005/0228305 A1 10/2005 Nagata et al.
2005/0267542 A1 * 12/2005 David .................. A61N 1/3622
607/17
2006/0030781 A1 2/2006 Shennib
2006/0264767 A1 11/2006 Shennib
2006/0284732 A1 12/2006 Brock-Fisher
2007/0249944 A1 10/2007 Fischell et al.
2007/0293775 A1 12/2007 Fischell et al.
2008/0058660 A1 3/2008 Fischell et al.
2008/0064973 A1 3/2008 Fischell et al.
2008/0139954 A1 6/2008 Day et al.
2008/0270036 A1 10/2008 Webb
2009/0054027 A1 2/2009 Jenkins
2009/0062670 A1 3/2009 Sterling et al.
2009/0076559 A1 3/2009 Libbus et al.
2009/0240156 A1 9/2009 Fischell et al.
2009/0322513 A1 12/2009 Hwang et al.
2010/0057152 A1 * 3/2010 Kim ..................... A61N 1/3621
600/518
2011/0105928 A1 5/2011 Bojovic et al.
2011/0112417 A1 5/2011 Gunderson et al.
2012/0190969 A1 * 7/2012 Kameli .............. A61N 1/39624
607/29
2012/0191150 A1 * 7/2012 Kameli ................ A61N 1/3787
607/4
2012/0191151 A1 * 7/2012 Kameli .................. A61N 1/378
607/6
2012/0191152 A1 * 7/2012 Kameli .................. A61N 1/375
607/7
2012/0220835 A1 8/2012 Chung
2012/0306652 A1 12/2012 Musiol et al.
2012/0330171 A1 12/2012 Zhang et al.
2014/0152436 A1 6/2014 Langer
2014/0163425 A1 6/2014 Tran
2015/0018658 A1 1/2015 Fischell et al.
2016/0008614 A1 1/2016 Zhang et al.
2016/0035204 A1 2/2016 Jansen
2016/0106378 A1 4/2016 Kyal et al.
2016/0128595 A1 5/2016 Fischell et al.
2016/0135706 A1 5/2016 Sullivan et al.
2016/0151021 A1 6/2016 Feng et al.
2016/0328950 A1 11/2016 Pelletier et al.
2017/0083667 A1 3/2017 Darrah et al.
2017/0330438 A1 11/2017 Howard et al.
2017/0354365 A1 * 12/2017 Zhou .................... A61B 5/0022
2018/0008159 A1 1/2018 Wang et al.
2018/0091657 A1 3/2018 Brown et al.
2018/0113986 A1 4/2018 Zhu
2018/0113987 A1 4/2018 Zhu
2018/0116537 A1 5/2018 Sullivan et al.
2018/0260706 A1 9/2018 Galloway et al.
2018/0301017 A1 10/2018 Dizengof et al.
2018/0318588 A1 * 11/2018 Dennis ................. A61N 1/3925
2019/0043616 A1 2/2019 Howard et al.
2019/0298201 A1 10/2019 Persen et al.
2019/0307328 A1 10/2019 Tran
2019/0328251 A1 10/2019 Jin
2019/0365269 A1 12/2019 Jun
2020/0008696 A1 1/2020 Sirendi et al.
2020/0038671 A1 2/2020 Schulhauser et al.
2020/0046241 A1 2/2020 Lam et al.
2020/0069245 A1 3/2020 Zhou
2020/0077892 A1 3/2020 Tran
2020/0108260 A1 4/2020 Haddad et al.
2020/0113459 A1 4/2020 Jäntti et al.

(56) References Cited

U.S. PATENT DOCUMENTS

| | | | |
|---|---|---|---|
| 2020/0160991 | A1 | 5/2020 | Smith et al. |
| 2020/0178821 | A1 | 6/2020 | Wu et al. |
| 2020/0337567 | A1 | 10/2020 | McCalmont et al. |
| 2020/0337581 | A1 | 10/2020 | Jung et al. |
| 2020/0352462 | A1 | 11/2020 | Pedalty et al. |
| 2020/0352466 | A1 | 11/2020 | Chakravarthy et al. |
| 2020/0357519 | A1 | 11/2020 | Chakravarthy et al. |
| 2020/0373005 | A1 | 11/2020 | Halsne et al. |
| 2020/0375458 | A1 | 12/2020 | Albert et al. |
| 2020/0390354 | A1 | 12/2020 | Huegerich et al. |
| 2021/0118562 | A1 | 4/2021 | Matos |
| 2021/0121090 | A1 | 4/2021 | Weinstein et al. |
| 2021/0138243 | A1 | 5/2021 | Zhang et al. |
| 2021/0138254 | A1 | 5/2021 | Matos |
| 2021/0154487 | A1 | 5/2021 | Bongberg et al. |
| 2021/0186329 | A1 | 6/2021 | Tran |
| 2021/0259560 | A1 | 8/2021 | Venkatraman et al. |
| 2021/0314756 | A1 | 10/2021 | Brooks et al. |
| 2021/0338134 | A1 | 11/2021 | Chakravarthy et al. |
| 2021/0338138 | A1 | 11/2021 | Pedalty et al. |
| 2021/0343132 | A1 | 11/2021 | Bonser |
| 2021/0343416 | A1 | 11/2021 | Chakravarthy et al. |
| 2021/0345934 | A1 | 11/2021 | Landgraf et al. |
| 2021/0353166 | A1 | 11/2021 | Sirendi et al. |
| 2021/0358631 | A1 | 11/2021 | Haddad et al. |
| 2022/0023626 | A1* | 1/2022 | Haddad .............. A61N 1/39622 |
| 2022/0039729 | A1 | 2/2022 | Fontanarava et al. |
| 2022/0051548 | A1 | 2/2022 | Pellegrini et al. |
| 2022/0095982 | A1 | 3/2022 | de Saint Victor et al. |
| 2022/0151533 | A1 | 5/2022 | Moon |
| 2022/0183607 | A1 | 6/2022 | Volosin et al. |
| 2022/0218259 | A1 | 7/2022 | Laversin et al. |
| 2022/0249026 | A1 | 8/2022 | Heneghan et al. |

FOREIGN PATENT DOCUMENTS

| | | | |
|---|---|---|---|
| CN | 106264518 4 | | 1/2017 |
| CN | 107874753 | A | 4/2018 |
| CN | 108039203 | A | 5/2018 |
| CN | 108324264 | A | 7/2018 |
| CN | 207924885 | U | 9/2018 |
| CN | 109009047 | A | 12/2018 |
| CN | 109820492 | A | 5/2019 |
| CN | 109953753 | A | 7/2019 |
| CN | 111667921 | A | 9/2020 |
| CN | 112515650 | A | 3/2021 |
| CN | 112515651 | A | 3/2021 |
| CN | 113080917 | A | 7/2021 |
| CN | 113598784 | A | 11/2021 |
| CN | 215128553 | U | 12/2021 |
| CN | 114711781 | A | 7/2022 |
| CN | 217014071 | U | 7/2022 |
| EP | 2644090 | | 10/2013 |
| ES | 2559263 | T3 | 2/2016 |
| FI | 128143 | B | 10/2019 |
| GB | 2590556 | A | 6/2021 |
| GB | 2600710 | A | 5/2022 |
| IN | 201811048444 | A | 12/2018 |
| JP | 3031277 | B2 | 4/2000 |
| JP | 2007289694 | A | 11/2007 |
| JP | 2009089883 | A | 4/2009 |
| JP | 6764830 | A | 12/2018 |
| JP | 2019129954 | A | 8/2019 |
| KR | 20030008655 | A | 1/2003 |
| KR | 100400212 | B1 | 11/2003 |
| KR | 20040107882 | A | 12/2004 |
| KR | 100637566 | B1 | 10/2006 |
| KR | 1020120118228 | A | 10/2012 |
| KR | 20200095605 | A | 8/2020 |
| KR | 102195189 | | 12/2020 |
| MX | 2016007079 | A | 11/2017 |
| SU | 442789 | A1 | 9/1974 |
| SU | 1042732 | A1 | 9/1983 |
| TR | 201719097 | A2 | 6/2019 |
| TW | M555707 | U | 2/2018 |
| TW | I669097 | B | 8/2019 |
| WO | 2010105053 | A3 | 1/2011 |
| WO | 2016034203 | A1 | 3/2016 |
| WO | 2018202606 | A1 | 11/2018 |
| WO | 2019110963 | A1 | 6/2019 |
| WO | 2020155078 | A1 | 8/2020 |
| WO | 2020226879 | A1 | 11/2020 |
| WO | 2020226881 | A1 | 11/2020 |
| WO | 2020226887 | A1 | 11/2020 |
| WO | 2021084535 | A1 | 5/2021 |
| WO | 2021133360 | A1 | 7/2021 |
| WO | 2021181389 | A1 | 9/2021 |
| WO | 2022034045 | A1 | 2/2022 |
| WO | 2022034480 | A1 | 2/2022 |
| WO | 2022070109 | A1 | 4/2022 |
| WO | 2022130152 | A1 | 6/2022 |

OTHER PUBLICATIONS

International Search Report and Written Opinion of International Application No. PCT/US2023/062304 dated May 11, 2023, 11 pp.

Kutyifa et al., “Use of the Wearable Cardioverter Defibrillator in High-Risk Cardiac Patients,” Circulation, vol. 132, No. 17, Oct. 27, 2015, pp. 1613-1619.

Schwartz et al., “Long QT syndrome, artificial intelligence, and common sense,” European Heart Journal, vol. 42, No. 38, Oct. 7, 2021, pp. 3962-3964.

* cited by examiner

PREDICTION OF VENTRICULAR TACHYCARDIA OR VENTRICULAR FIBRILLATION TERMINATION TO LIMIT THERAPIES AND EMERGENCY MEDICAL SERVICE OR BYSTANDER ALERTS

This application is a national stage application under 35 U.S.C. § 371 of PCT Application No. PCT/US2023/062304, filed Feb. 9, 2023, which claims the benefit of U.S. Provisional Application Ser. No. 63/267,823, filed Feb. 10, 2022, which are each hereby incorporated by reference in their entirety.

FIELD

This disclosure generally relates to systems including medical devices and, more particularly, to monitoring of patient health using such systems.

BACKGROUND

A variety of devices are configured to configured to monitor physiological signals of a patient. Such devices include implantable or wearable medical devices, as well as a variety of wearable health or fitness tracking devices. The physiological signals sensed by such devices include as examples, electrocardiogram (ECG) signals, respiration signals, perfusion signals, activity and/or posture signals, pressure signals, blood oxygen saturation signals, body composition, and blood glucose or other blood constituent signals. In general, using these signals, such devices facilitate monitoring and evaluating patient health over a number of months or years, outside of a clinic setting.

In some cases, such devices are configured to detect health events, including acute health events, based on the physiological signals, such as episodes of cardiac arrhythmia, myocardial infarction, stroke, falls, or seizure. Example arrhythmia types include cardiac arrest (e.g., asystole), ventricular tachycardia (VT), and ventricular fibrillation (VF). The devices may store ECG and other physiological signal data collected during a time period including an episode as episode data. Such acute health events are associated with significant rates of death, particularly if not treated quickly.

For example, VF and other malignant tachyarrhythmias are the most commonly identified arrhythmia in sudden cardiac arrest (SCA) patients. If this arrhythmia continues for more than a few seconds, it may result in cardiogenic shock and cessation of effective blood circulation. The survival rate from SCA decreases between 7 and 10 percent for every minute that the patient waits for defibrillation. Consequently, sudden cardiac death (SCD) may result in a matter of minutes.

SUMMARY

In general, the disclosure describes techniques for determining whether a cardiac event is likely to self-terminate within a reasonable period of time and responding to the situation based on such a determination. For example, sensing circuitry of an implantable medical device (IMD) may sense an indication that an acute health event, such as a cardiac event, is occurring in the patient. Processing circuitry of a medical device system, such as the IMD, computing device(s), Internet of Things (IoT) device(s), or other devices may analyze the indication and determine whether the cardiac event is likely to self-terminate within a predetermined period of time. If the cardiac event is likely to self-terminate within the predetermined period of time, the medical device system may refrain from treating the patient and/or issuing an alert. If the cardiac event is unlikely to self-terminate within the predetermined period of time, the medical device system may treat the patient and/or issue the alert. As such, the techniques of this disclosure may affect the treatment of an acute health event and/or issue an alert, facilitating the treatment (e.g., more appropriate treatment) of an acute health event, thereby improving patient outcomes, patient safety, and/or patient comfort.

The techniques of this disclosure may provide for the more accurate determination of situations in which a treatment, such as a shock to the heart, may be desirable. In view of the above, the present disclosure describes a technological improvement or a technical solution that is integrated into a practical application and an improvement to the functioning of medical systems including medical devices.

Unlike conventional acute health event detection systems, the techniques and systems of this disclosure may determine that a cardiac event is unlikely to self-terminate prior to delivering therapy or issuing an alert. A medical system that determines that a cardiac event is unlikely to self-terminate and, in response thereto, delivers therapy or issues an alert may provide one or more technical and clinical advantages. For example, such a medical system may not deliver (or refrain from delivering therapy) in a situation where the cardiac event is likely to self-terminate, thereby avoiding the delivery of therapy which may not be desirable for patient comfort and/or power conservation. Additionally, such a medical system may not issue an alert (or refrain from issuing an alert) in a situation where the cardiac event is likely to self-terminate, thereby avoiding the alerting of caregivers, emergency personnel, or other medical personnel, thereby decreasing the burden on such people and diversion of resources from other patients.

In some examples, a medical system that determines that a cardiac event is unlikely to self-terminate and, in response thereto, delivers therapy or issues an alert may use a machine learning model to more accurately determine whether a cardiac event is likely to self-terminate. In some examples, the machine learning model is trained with a set of training data. This set of training data may include historical sensed physiological parameters, history of self-termination status of cardiac events, and/or historical information about the patient. Such data may indicate relationships between sensed physiological parameters and a likelihood that a cardiac event will self-terminate. Because the machine learning model may be trained with a large volume of training data, the machine learning model may reduce the number of times a medical device system may deliver therapy and/or send an alert when such therapy and/or alert may not be desirable when compared to conventional medical device systems.

Additionally, the techniques and systems of this disclosure may be implemented in (or partially implemented in) an implantable medical device (IMD) that can continuously (e.g., on a periodic or triggered basis without human intervention) sense physiological parameters while subcutaneously implanted in a patient over months or years and perform numerous operations per second on patient data (such as physiological parameters) to enable the systems herein to detect acute health events, such as cardiac events. Using techniques of this disclosure with an IMD may be advantageous when a physician cannot be continuously present with the patient over weeks or months to evaluate the physiological parameters and/or where performing the operations on the physiological parameters described herein (e.g., application of a machine learning model, delivering therapy, issuing an alert, etc.) on weeks or months of physiological parameter data could not practically be performed in the mind of a physician.

In one example, a medical device system includes an implantable medical device (IMD) configured to sense physiological parameters of a patient; memory configured to store current sensed physiological parameters of the patient; and processing circuitry communicatively coupled to the memory, the processing circuitry being configured to: determine, based on the current sensed physiological parameters of the patient, that a cardiac event is occurring in the patient; determine, based on the current sensed physiological parameters of the patient, that the cardiac event is unlikely to self-terminate within a predetermined period of time; and deliver, in response to determining that the cardiac event is unlikely to self-terminate, therapy to the patient or issue an alert.

In one example, a method includes determining, by processing circuitry and based on current sensed physiological parameters of a patient, that a cardiac event is occurring in the patient; determining, by the processing circuitry and based on the current sensed physiological parameters of the patient, that the cardiac event is unlikely to self-terminate within a predetermined period of time; and in response to determining that the cardiac event is unlikely to self-terminate, deliver therapy to the patient or issue an alert.

In another example, a medical device system is configured to implement any of the techniques of this disclosure.

In another example, a non-transitory computer-readable storage medium stores instructions that, when executed, cause processing circuitry to perform any of the techniques of this disclosure.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

BRIEF DESCRIPTION OF DRAWINGS

Like reference characters refer to like elements throughout the figures and description.

DETAILED DESCRIPTION

Figure 1:
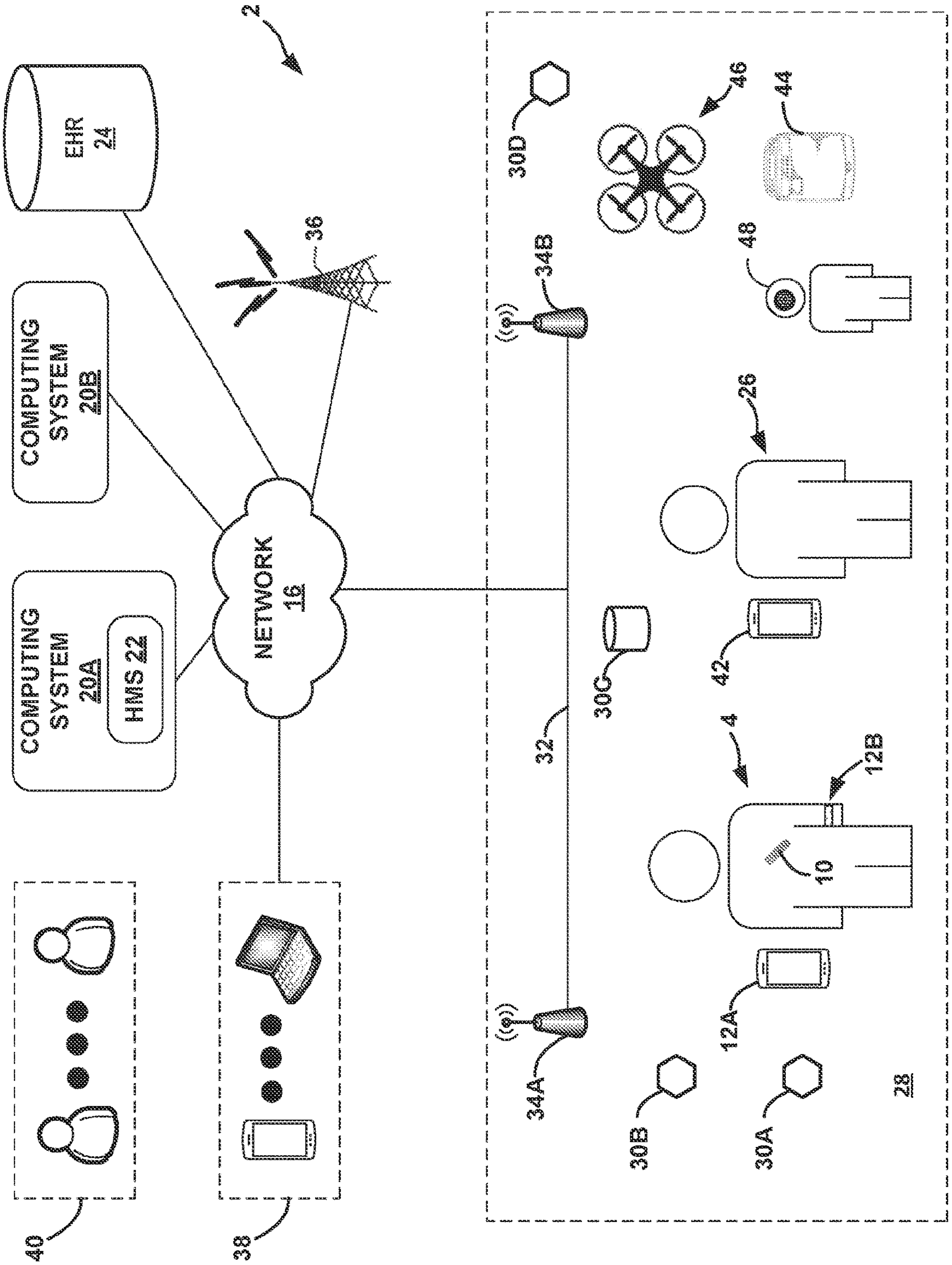
FIG. 1 is a block diagram illustrating an example system configured detect acute health events of a patient, and to respond to such detections, in accordance with one or more techniques of this disclosure.

A patient who is living alone may have an acute health event, such as sudden cardiac arrest, stroke, acute myocardial infarction, or anaphylactic shock, and become incapacitated. In the incapacitated state, the patient may not be able to make a phone call to an emergency service, such as 911 in the United States of America, to obtain medical help. Since no other person may be around to confirm the medical situation and call the emergency service, the patient may not be able to obtain the medical help that is necessary for the well-being of the patient.

A variety of types of implantable and computing devices are configured detect arrhythmia episodes and other acute health events based on sensed ECGs and, in some cases, other physiological signals. Computing devices that may be used to non-invasively sense and monitor ECGs and other physiological signals include wearable devices with electrodes configured to contact the skin of the patient, such as patches, chest belts, vests, watches, or necklaces, and other non-contact monitoring devices, such as devices configured to monitor sound, radar, light, images, etc. Such computing devices may facilitate relatively longer-term monitoring of patient health during normal daily activities.

Implantable medical devices (IMDs) also sense and monitor ECGs and other physiological signals, and detect acute health events such as episodes of arrhythmia, cardiac arrest, myocardial infarction, stroke, and seizure. For examples, IMDs may include sensors, such as sound sensors which may sense heart sounds, accelerometers (e.g., 3-axis accelerometers), impedance sensors, optical sensors, etc., which may be used to determine the mechanical function of the heart or, in general, the physical condition of the patient. For example, impedance may be used to sense a respiratory rate or effort of a patient. If the respiratory rate or effort of the patient does not deteriorate over time, that might be an indicator that the heart rhythm is stable and a cardiac event may be more likely to self-terminate. In a similar manner, a pulse or pulse rate may be sensed using an impedance sensor or an optical sensor, and gait, posture, and/or activity may be sensed using a 3-axis accelerometer. Signals from such sensors may be indicative of whether a cardiac event may self-terminate. Example IMDs include pacemakers and implantable cardioverter-defibrillators, which may be coupled to intravascular or extravascular leads, as well as pacemakers with housings configured for implantation within the heart, which may be leadless. Some IMDs do not provide therapy, such as implantable patient monitors. One example of such an IMD is the Reveal LINQ™ Insertable Cardiac Monitor (ICM) or the LINQ II™ ICM, available from Medtronic plc, which may be inserted subcutaneously.

Such IMDs may facilitate relatively longer-term monitoring of patients during normal daily activities, and may periodically transmit collected data, e.g., episode data for detected arrhythmia episodes, to a remote patient monitoring system, such as the Medtronic Carelink™ Network.

Such an IMD may interact with other devices. The IMD may sense an indication of an acute health event of the patient. These other devices may be verification devices or part of a verification system and may be configured to verify whether the patient actually experienced the sensed acute health event. For example, the verification device or system may verify the acute health event. Based on the verification of the acute health event, the verification device or system, or the IMD, may send an alert regarding the acute health event, such as call an emergency service. The verification device or system may include at least one of a smartphone, wearable device, video camera, infrared camera, thermal camera, radar system, sonar system, lidar system, bed sensor, smart speaker, smart television, drone, robot, or other IoT device(s).

FIG. 1 is a block diagram illustrating an example system 2 configured detect acute health events of a patient 4, and to respond to such detection, in accordance with one or more techniques of this disclosure. As used herein, the terms "detect," "detection." and the like, may refer to detection of an acute health event presently (at the time the data is collected) being experienced by patient 4, as well as detection, based on the collected data, that the condition of patient 4 is such that patient 4 has a suprathreshold likelihood of experiencing the acute health event within a particular timeframe, e.g., a prediction of the acute health event. The example techniques may be used with one or more patient sensing devices, e.g., IMD 10, which may be in wireless communication with one or more patient computing devices, e.g., patient computing devices 12A and 12B (collectively, "computing devices 12"). Computing devices 12 may be verification devices and may attempt to verify the occurrence of an acute health event. Although not illustrated in FIG. 1, IMD 10 include electrodes and other sensors to sense physiological signals of patient 4, and may collect and store sensed physiological data based on the signals, and may detect episodes based on the data.

In some examples, although not depicted in FIG. 1, patient 4 may have a plurality of patient sensing devices, such as IMD 10. In some examples, the plurality of patient sensing devices may communicate with each other and/or computing device(s) 12. In some examples, the plurality of patient sensing devices may use time matching techniques, such determining a difference in a clock of each patient sensing device and applying the difference when saving a time of occurrence of a sensed indication of an acute health event, or use a common clock. In this manner, sensed indications of acute health events of different patient sensing devices may be synchronized. In another example, one patient sensing device may be configured as a master and other patient sensing devices may be configured as slaves.

IMD 10 may be implanted outside of a thoracic cavity of patient 4 (e.g., subcutaneously in the pectoral location illustrated in FIG. 1). IMD 10 may be positioned near the sternum near or just below the level of the heart of patient 4, e.g., at least partially within the cardiac silhouette. In some examples, IMD 10 takes the form of the LINQ™ ICM. Although described primarily in the context of examples in which IMD 10 takes the form of an ICM, the techniques of this disclosure may be implemented in systems including any one or more implantable or external medical devices, including monitors, pacemakers, defibrillators, wearable external defibrillators, neurostimulators, or drug pumps. Furthermore, although described primarily in the context of examples including a single implanted patient sensing device, in some examples a system includes one or more patient sensing devices, which may be implanted within patient 4 or external to (e.g., worn by) patient 4.

The example of FIG. 1 includes environment 28. Environment 28 may be a home, office, or place of business, or public venue, as examples. Computing devices 12 are configured for wireless communication with IMD 10. Computing devices 12 retrieve or receive event data and other sensed physiological data from IMD 10 that was collected and stored by IMD 10. In some examples, computing devices 12 take the form of personal computing devices of patient 4. For example, computing device 12A may take the form of a smartphone of patient 4, and computing device 12B may take the form of a smartwatch or other smart apparel of patient 4. In some examples, computing devices 12 may be any computing device configured for wireless communication with IMD 10, such as a desktop, laptop, or tablet computer. Computing devices 12 may communicate with IMD 10 and each other according to the Bluetooth®, Bluetooth® Low Energy (BLE), or other wireless communication protocols, as examples. In some examples, only one of computing devices 12, e.g., computing device 12A, is configured for communication with IMD 10, e.g., due to execution of software (e.g., part of a health monitoring application as described herein) enabling communication and interaction with an IMD. In some examples, computing device(s) 12 may be configured to receive an indication of an acute health event of patient 4 from IMD 10.

In some examples, computing device(s) 12, e.g., wearable computing device 12B in the example illustrated by FIG. 1A, may include electrodes and other sensors to sense physiological signals of patient 4, and may collect and store physiological data and detect episodes based on such signals. Computing device 12B may be incorporated into the apparel of patient 14, such as within clothing, shoes, eyeglasses, a watch, ring, necklace, wristband, a hat, etc. In some examples, computing device 12B is a smartwatch or other accessory or peripheral for a smartphone computing device 12A.

One or more of computing devices 12 may be configured to communicate with a variety of other devices or systems via a network 16. For example, one or more of computing devices 12 may be configured to communicate with one or more computing systems, e.g., computing systems 20A and 20B (collectively, "computing systems 20") via network 16. Computing systems 20A and 20B may be respectively managed by manufacturers of IMD 10 and computing devices 12 to, for example, provide cloud storage and analysis of collected data, maintenance and software services, or other networked functionality for their respective devices and users thereof. Computing system 20A may comprise, or may be implemented by, the Medtronic Carelink™ Network, in some examples. In the example illustrated by FIG. 1, computing system 20A implements a health monitoring system (HMS) 22, although in other examples, either of both of computing systems 20 may implement HMS 22. As will be described in greater detail below, HMS 22 facilities detection of acute health events of patient 4 by system 2, and the responses of system 2 to such acute health events.

Computing device(s) 12 may transmit data, including data retrieved or received from IMD 10, to computing system(s) 20 via network 16. The data may include sensed data, e.g., values of physiological parameters measured by IMD 10 and, in some cases one or more of computing devices 12, data regarding episodes of arrhythmia or other acute health events detected by IMD 10 and/or computing device(s) 12, and other physiological signals or data recorded by IMD 10 and/or computing device(s) 12. HMS 22 may also retrieve data regarding patient 4 from one or more sources of electronic health records (EHR) 24 via network. EHR 24 may include data regarding historical (e.g., baseline) physiological parameter values, previous health events and treatments, disease states, comorbidities, demographics, height, weight, and/or body mass index (BMI), as examples, of patients including patient 4. HMS 22 may use data from EHR 24 to configure algorithms implemented by IMD 10 and/or computing devices 12 to detect acute health events for patient 4. In some examples, HMS 22 provides data from EHR 24 to computing device(s) 12 and/or IMD 10 for storage therein and use as part of their algorithms for detecting acute health events.

Network 16 may include one or more computing devices, such as one or more non-edge switches, routers, hubs, gateways, security devices such as firewalls, intrusion detection, and/or intrusion prevention devices, servers, cellular base stations and nodes, wireless access points, bridges, cable modems, application accelerators, or other network devices. Network 16 may include one or more networks administered by service providers, and may thus form part of a large-scale public network infrastructure, e.g., the Internet. Network 16 may provide computing devices and systems, such as those illustrated in FIG. 1, access to the Internet, and may provide a communication framework that allows the computing devices and systems to communicate with one another. In some examples, network 16 may include a private network that provides a communication framework that allows the computing devices and systems illustrated in FIG. 1 to communicate with each other, but isolates some of the data flows from devices external to the private network for security purposes. In some examples, the communications between the computing devices and systems illustrated in FIG. 1 are encrypted.

As will be described herein, IMD 10 may be configured to detect acute health events of patient 4 based on data sensed by IMD 10 and, in some cases, other data, such as data sensed by computing devices 12A and/or 12B, and/or data from EHR 24. In response to detection of an acute health event. IMD 10 may wirelessly transmit an indication of the acute health event, such as a message, to one or both of computing devices 12A and 12B. The message may indicate that IMD 10 detected an acute health event of patient 4. The message may indicate a time that IMD 10 detected the acute health event. The message may include physiological data collected by IMD 10, e.g., data which lead to detection of the acute health event, data prior to detection of the acute health event, and/or real-time or more recent data collected after detection of the acute health event. The physiological data may include values of one or more physiological parameters and/or digitized physiological signals. Some examples of acute health events are cardiac arrest, ventricular fibrillation, ventricular tachycardia, myocardial infarction, pause in heat rhythm (asystole), pulseless electrical activity (PEA), acute respiratory distress syndrome (ARDS), stroke, seizure, fall, anaphylactic shock, or respiratory failure.

In some examples, any of, or any combination of, computing device(s) 12, Internet of Things (IoT) devices, such as IoT devices 30A-30D (collectively "IoT devices 30"), drone 46, or robot 48 may be verification devices or part of a verification system. The verification device or system may attempt to verify the acute health event. For example, the verification device or system may determine physiological parameters of patient 4 and may determine whether the physiological parameters of patient 4 meet predefined criteria. The predefined criteria may be indicative of the acute health event.

For example, environment 28 may include a plurality of cameras (e.g., any of IoT devices 30). The plurality of cameras may be located throughout a house, for example, and may be used to determine a location of patient 4 and/or to verify the acute health event. In some examples, one or more cameras are only activated by the verification device or system for locating patient 4 or verifying the acute health event in certain instances. For example, a camera may only be activated if the sensed indication of the acute health event is sufficiently strong. For example, strength of the indication may be scored by IMD 10 or computing device(s) 12, and the camera may only be activated if the score is equal to or higher than a predetermined score.

In some examples, environment 28 includes a house. IoT devices 30 may determine whether patient 4 is inside the house or outside the house. For example, IoT devices 30 may include a smart speaker, smart lock(s), and/or cameras that may monitor a location of patient 4. Processing circuitry of IoT devices 30, computing devices 12, and/or IMD 10 may determine the location of patient 4 based on the monitoring. The processing circuitry may use the determined location to dispatch drone 46 and/or robot 48 to the location of patient 4.

In some examples, drone 46 or robot 48 may navigate to the proximity of patient 4 to determine physiological parameters of patient 4. In some examples, cameras may capture video, infrared, thermal, or other images of patient 4. The images may be processed to identify physiological parameters of patient 4. For example, the verification device or system may determine posture and facial features of patient 4 through the use of captured images. In some examples, the verification device or system may use facial recognition techniques on one or more images to detect changes in a face of patient 4, such as a droop, that may be a side effect of a stroke.

Infrared cameras, radar systems, sonar systems, lidar systems or other sensors may measure the presence or absence of a pulse, oxygen saturation levels, or breathing of patient 4 when attempting to verify the acute health event. The absence of a pulse, reduced oxygen saturation, the absence of breathing, or convulsions may each be used to verify the acute health event. For example, one of more of IoT devices 30 may be configured to sense heartbeat sounds and the verification device or system may use the heart beat sounds to determine a heartbeat or pulse (or absence thereof) of patient 4. In some examples, the verification device or system may use radar, lidar, sonar, or cameras to determine respiration rate of patient 4 or changes in surfaces of patient 4, for example, by monitoring changes in the position of chest of patient 4 over time. In some examples, the verification device or system may use a camera to sense blood flow in patient 4 (e.g., using a red-sensitive image of a face of patient 4, or other exposed skin of patient 4). In other examples, the verification device or system may use radar, sonar, or lidar to identify area of interest on patient 4 and analyze a sequence of images from a camera over time to sense blood flow in patient 4. In some examples, the verification device or system may include an oxygen sensor, which may be integrated into computing device 12B, for example, which may be configured to monitor an oxygen saturation level of blood of patient 4. In some examples, the verification device or system may use traditional signal processing or machine learning techniques to combine measurements from multiple sensors to verify the acute health event.

In some examples, in response to the message indicative of the sensing of the acute health event from IMD 10, computing device(s) 12 may prompt patient 4 to provide a response. For example, computing device(s) 12 may audibly ask the patient if they are okay or may ask the patient to provide tactile input indicating that they are okay in an attempt to elicit a response. Computing device(s) 12 may wait for a response from patient 4. After a predetermined period of time, which may be on the order of up to 60 seconds, if the patient has not responded, computing device(s) 12 may attempt to verify the acute health event. For example, computing device 12B may attempt to take a pulse of patient 4.

Other devices in the environment 28 of patient 4 may also be configured to verify the acute health event. For example, environment 28 may include one or more Internet of Things (IoT) devices, such as IoT devices 30A-30D (collectively "IoT devices 30") illustrated in the example of FIG. 1. IoT devices 30 may include, as examples, so called "smart" speakers, cameras, lights, locks, thermostats, appliances, actuators, controllers, or any other smart home (or building) devices. For example, IoT devices 30 may include video cameras, infrared cameras, thermal cameras, radar systems, sonar system, lidar systems, bed sensors, smart speaker, smart television, or other IoT devices. These IoT devices 30 may be configured to determine physiological parameters of patient 4. For example, IoT devices 30 may be configured to determine at least one of pulse rate, blood perfusion, breathing rate, breathing intensity, posture, facial features, color of a face, or an electrocardiogram.

In some examples, IoT devices 30 or computing device(s) 12 may be configured to determine a location of patient 4. For example, a camera may capture an image and image processing techniques may be used to determine that patient 4 is in a captured image. A radar, sonar, or lidar system may transmit radio, sound, or light waves, respectively, and measure reflections of those waves to determine a location of patient 4. Bed sensors may determine that patient 4 is in bed based on pressure placed on the bed sensors. In some examples, computing device(s) 12 may receive, from IoT devices 30, information indicative of the location of patient 4 and may process such information to determine the location of patient 4.

As mentioned above, in some examples, IoT devices 30 may include bed sensors. Bed sensors may be useful in verifying the acute health event as lethal acute health events frequently occur during sleep. In some examples, IoT devices 30 may include a device, such as a camera, that is configured to monitor the behavior of patient 4. For example, the device may capture images of patient 4 and processing circuitry may perform image analysis to determine a location of patient 4 or physiological parameters of patient 4. In some examples, IoT devices 30 may include a device, such as a radar system, that is configured to monitor sleep apnea of patient 4. For example, a radar system, may transmit radio waves and measure reflections of the radio waves to monitor sleep apnea. Reflections of the radio waves may show relatively consistent movement of the chest of patient 4 when breathing normally. Reflections of the radio waves may show more erratic movement of the chest of patient 4 during a sleep apnea episode, where patient 4 may pause breathing and then gasp for air.

In the example of FIG. 1, IoT device 30C is a smart speaker and/or controller, which may include a display. In some examples, rather than computing device(s) 12 attempting to solicit the response from patient 4, IoT device 30C may attempt to solicit the response. IoT devices 30 may provide audible and/or visual alarms when configured with output devices to do so. As other examples, IoT devices 30 (or computing device(s) 12) may cause smart lights throughout environment 28 to flash or blink, and/or unlock or open smart locks on doors of the house. By opening smart locks, IoT devices 30 or computing device(s) 12 may facilitate quick entry into the home by emergency medical systems (EMS) personnel or bystander 26. In some examples, IoT devices 30 that include cameras or other sensors may activate those sensors to collect data regarding patient 4, e.g., for evaluation or verification of the condition of patient 4 and, in some examples, a location of patient 4.

In some examples, drone 46 may be an unmanned aerial vehicle (UAV). Drone 46 may be equipped with a number of sensors and/or actuators to perform a number of operations, such as determine physiological parameters of patient 4. For example, drone 46 may include a camera or other sensors to navigate to its intended location, identify patient 4 and, in some cases, bystander 26, and to evaluate or verify a condition of patient. In some examples, drone 46 may be configured to determine the location of patient 4, such as through camera images captured by drone 46 or other techniques. In some examples, drone 46 may include user interface devices to communicate with patient 4 and/or bystander 26. In some examples, drone 46 may provide directions to bystander 26, to the location of patient 4 and regarding how to provide first responder care, such as cardio-pulmonary resuscitation (CPR), to patient 4. In some examples, drone 46 may carry medical equipment, e.g., automated external defibrillator (AED) 44, and/or medication to the location of patient 4.

In some examples, robot 48 may be equipped with a number of sensors and/or actuators to perform a number of operations, such as determine physiological parameters of patient 4. For example, robot 48 may include a camera or other sensors to navigate to its intended location, identify patient 4 and, in some cases, bystander 26, and to evaluate a condition of patient. In some examples, robot 48 may be configured to determine the location of patient 4, such as through camera images captured by robot 48, audio captured by robot 48, or other techniques. In some examples, robot 48 may include user interface devices to communicate with patient 4 and/or bystander 26. In some examples, robot 48 may provide directions to bystander 26, to the location of patient 4 and/or instructions regarding how to provide first responder care, such as CPR, to patient 4. In some examples, robot 48 may carry or include medical equipment, e.g., AED 44, and/or medication which robot 48 may bring to the location of patient 4. In some examples, robot 48 may perform a medical intervention on patient 4, such as perform CPR or defibrillation on patient 4, or perform some other medical treatment.

In some examples, in response to the message from IMD 10, computing device(s) 12 may also output an alarm that may be visual and/or audible, and configured to immediately attract the attention of patient 4 or any person in environment 28 with patient 4, e.g., a bystander 26. Computing device(s) 12 may also transmit a message to HMS 22 via network 16. The message may include the data received from IMD 10 and, in some cases, additional data collected by computing device(s) 12 or other devices in response to the detection of the acute health event by IMD 10. For example, the message may include a location of patient 4 determined by computing device(s) 12, IoT devices 30A-30D, drone 46, or robot 48.

Computing device(s) 12 may be configured to wirelessly communicate with IoT devices 30 to cause IoT devices 30 to take the actions described herein. In some examples, HMS 22 communicates with IoT devices 30 via network 16 to cause IoT devices 30 to take the actions described herein, e.g., in response to receiving the alert message from computing device(s) 12 as described above. In some examples, IMD 10 is configured to communicate wirelessly with one or more of IoT devices 30. e.g., in response to detection of an acute health event when communication with computing devices 12 is unavailable or not preferred. In such examples, IoT device(s) 30 may be configured to provide some or all of the functionality ascribed to computing devices 12 herein.

Environment 28 includes computing facilities, e.g., a local network 32, by which IMD 10, computing devices 12. IoT devices 30, and other devices within environment 28 may communicate via network 16, e.g., with HMS 22. For example, environment 28 may be configured with wireless technology, such as 802.11 wireless networks, 802.15 ZigBee networks, an ultrawideband protocol, near-filed communication, or the like. Environment 28 may include one or more wireless access points, e.g., wireless access points 34A and 34B (collectively, "wireless access points 34") that provide support for wireless communications throughout environment 28. Additionally, or alternatively, e.g., when local network is unavailable, IMD 10, computing devices 12, IoT devices 30, and other devices within environment 28 may be configured to communicate with network 16, e.g., with HMS 22, via a cellular base station 36 and a cellular network.

Computing device(s) 12, and in some examples IoT devices 30, may include input devices and interfaces to allow a user to override the alarm in the event the detection of the acute health event by IMD 10 was false. In some examples, one or more of computing device(s) 12 and IoT device(s) 30 may implement an event assistant. The event assistant may provide a conversational interface or a tactile interface for patient 4 and/or bystander 26 to exchange information with the computing device or IoT device. The event assistant may query the user regarding the condition of patient 4 in response to receiving the alert message from IMD 10. Responses from the user may be used to confirm or override detection of the acute health event by IMD 10, or to provide additional information about the acute health event or the condition of patient 4 more generally that may improve the efficacy of the treatment of patient 4. For example, information received by the event assistant may be used to provide an indication of severity or type (e.g., differential diagnosis) for the acute health event. The event assistant may use natural language processing and context data to interpret utterances by the user. In some examples, in addition to receiving responses to queries posed by the assistant, the event assistant may be configured to respond to queries posed by the user. For example, patient 4 may indicate that they feel dizzy and ask the event assistant, "how am I doing?"

In some examples, computing device(s) 12 and/or HMS 22 may implement one or more algorithms to evaluate the sensed physiological data received from IMD 10, and in some cases additional physiological or other data sensed or otherwise collected by computing device(s) 12 and/or IoT devices 30, to confirm or override the detection of the acute health event by IMD 10. In some examples, computing device(s) 12 and/or computing system(s) 20 may have greater processing capacity than IMD 10, enabling more complex analysis of the data. In some examples, the computing device(s) 12 and/or HMS 22 may apply the data to a machine learning model or other artificial intelligence developed algorithm, e.g., to determine whether the data is sufficiently indicative of the acute health event.

In examples in which computing device(s) 12 are configured to perform an acute health event confirmation analysis or verification, computing device(s) 12 may transmit alert messages to HMS 22 and/or IoT devices 30 in response to confirming or verifying the acute health event. In some examples, computing device(s) 12 may be configured to transmit the alert messages prior to completing the confirmation or verification analysis, and transmit cancellation messages in response to the analysis overriding the detection of the acute health event by IMD 10. HMS 22 may be configured to perform a number of operations in response to receiving an alert message from computing device(s) 12 and/or IoT device(s) 30. HMS 22 may be configured to cancel such operations in response to receiving a cancellation message from computing device(s) 12 and/or IoT device(s) 30.

In some examples, computing device(s) 12 may transmit the alert to a care provider, an emergency medical technician, or other designated persons in environment 28 or near environment 28. For example, the alert may be a communication to the emergency medical technician, or local neighborhood alert system with an automated emergency defibrillator service, to a care provider, etc. In some examples, the alert includes collected data from IMD 10 and the verification device or system, such that medical personnel may be prepared to take quick action on arrival in environment 28. In some examples, the alert includes at least one of a telephone call, a short message service message, an email, a web alert, a security system alert, a social media alert, an audible alert, or a visual alert.

In some examples, the verification device or system may send an alert through a security system (which may include one or more of IoT devices 30) in environment 28 to flash a "save our souls" (SOS) message, sound an audible alarm, or the like. In some examples, the verification device or system may notify neighbors of patient 4 of a medical emergency. In some examples, the verification system may send an alarm or warning to everyone and every device around the environment 28. For example, the verification device or system may send an audible warning to IoT device 30C (the smart speaker). In some examples, the verification device or system may send an alarm to a social media group or group email, for example, where there is a geographic or therapy relevance to patient 4.

For example, HMS 22 may be configured to transmit alert messages to one or more computing devices 38 associated with one or more care providers 40 via network 16. Care providers may include EMS and hospitals, and may include particular departments within a hospital, such as an emergency department, catheterization lab, or a stroke response department. Computing devices 38 may include smartphones, desktop, laptop, or tablet computers, or workstations associated with such systems or entities, or employees of such systems or entities. The alert messages may include any of the data collected by IMD 10, computing device(s) 12, and IoT device(s) 30, including sensed physiological parameters, time of the acute health event, location of patient 4, and results of the analysis by IMD 10, computing device(s) 12, IoT device(s) 30, and/or HMS 22. The information transmitted from HMS 22 to care providers 40 may improve the timeliness and effectiveness of treatment of the acute health event of patient 4 by care providers 40. In some examples, instead of, or in addition to, HMS 22 providing an alert message to one or more computing devices 38 associated with an EMS care provider 40, computing device(s) 12 and/or IoT devices 30 may be configured to automatically contact EMS, e.g., autodial 911 (e.g., in the United States or North America to use the telephone system to contact a 911 call center), in response to receiving an alert message from IMD 10. Again, such operations may be cancelled by patient 4, bystander 26, or another user via a user interface of computing device(s) 12 or IoT device(s) 30, or automatically cancelled by computing device(s) 12 based on a confirmatory analysis or verification performed by the computing device(s) overriding the detection of the acute health event by IMD 10.

Similarly, HMS 22 may be configured to transmit an alert message to computing device 42 of bystander 26, which may improve the timeliness and effectiveness of treatment of the acute health event of patient 4 by bystander 26. Computing device 42 may be similar to computing devices 12 and computing devices 38, e.g., a smartphone. In some examples, HMS 22 may determine that bystander 26 is proximate to patient 4 based on a location of patient 4, e.g., received from computing device(s) 12, and a location of computing device 42, e.g., reported to HMS 22 by an application implemented on computing device 42. In some examples, HMS 22 may transmit the alert message to any computing devices 42 in an alert area determined based on the location of patient 4, e.g., by transmitting the alert message to all computing devices in communication with base station 36.

In some examples, the alert message to bystander 26 may be configured to assist a layperson in treating patient. For example, the alert message to bystander 26 may include a location (and in some cases a description) of patient 4, the general nature of the acute health event, directions for providing care to patient 4, such as directions for providing CPR, a location of nearby medical equipment for treatment of patient 4, such as an automated external defibrillator (AED) 44 or life vest, and instructions for use of the equipment. In some examples, computing device(s) 12, IoT device(s) 30, and/or computing device 42 may implement an event assistant configured to use natural language processing and context data to provide a conversational interface for bystander 26. The assistant may provide bystander 26 with directions for providing care to patient 4, and respond to queries from bystander 26 about how to provide care to patient 4.

In some examples, HMS 22 may mediate bi-directional audio (and in some cases video) communication between care providers 40 and patient 4 and/or bystander 26. Such communication may allow care providers 40 to evaluate the condition of patient 4, e.g., through communication with patient 4 and/or bystander 26, or through use of a camera or other sensors of the computing device(s) 12 or IoT device(s) 30, in advance of the time they will begin caring for the patient, which may improve the efficacy of care delivered to the patient. Such communication may also allow the care providers to instruct bystander 26 regarding first responder treatment of patient 4.

In some examples, HMS 22 may control dispatch of drone 46 to environment 28, or a location near environment 28 or patient 4. Drone 46 may be an unmanned aerial vehicle (UAV). Drone 46 may be equipped with a number of sensors and/or actuators to perform a number of operations. For example, drone 46 may include a camera or other sensors to navigate to its intended location, identify patient 4 and, in some cases, bystander 26, and to evaluate a condition of patient. In some examples, drone 46 may include user interface devices to communicate with patient 4 and/or bystander 26. In some examples, drone 46 may provide directions to bystander 26, to the location of patient 4, and/or instructions regarding how to provide first responder care, such as CPR, to patient 4. In some examples, drone 46 may carry medical equipment, e.g., AED 44, and/or medication to the location of patient 4.

In some examples, HMS 22 may control dispatch of robot 48 to environment 28, or a location near environment 28 or patient 4. Robot 48 may be equipped with a number of sensors and/or actuators to perform a number of operations. For example, robot 48 may include a camera or other sensors to navigate to its intended location, identify patient 4 and, in some cases, bystander 26, and to evaluate a condition of patient, such as taking an ECG or measuring a pulse. In some examples, robot 48 may act as an AED by touching two parts of the body of patient 4 with extendable arms having electrodes. In some examples, robot 48 may include user interface devices to communicate with patient 4 and/or bystander 26. In some examples, robot 48 may provide directions to bystander 26, to the location of patient 4, and/or instructions regarding how to provide first responder care, such as CPR, to patient 4. In some examples, robot 48 may carry medical equipment, e.g., AED 44, and/or medication to the location of patient 4. In some examples, robot 48 may perform a medical intervention on patient 4, such as perform CPR or defibrillation on patient 4, or perform some other medical treatment.

Figure 2:
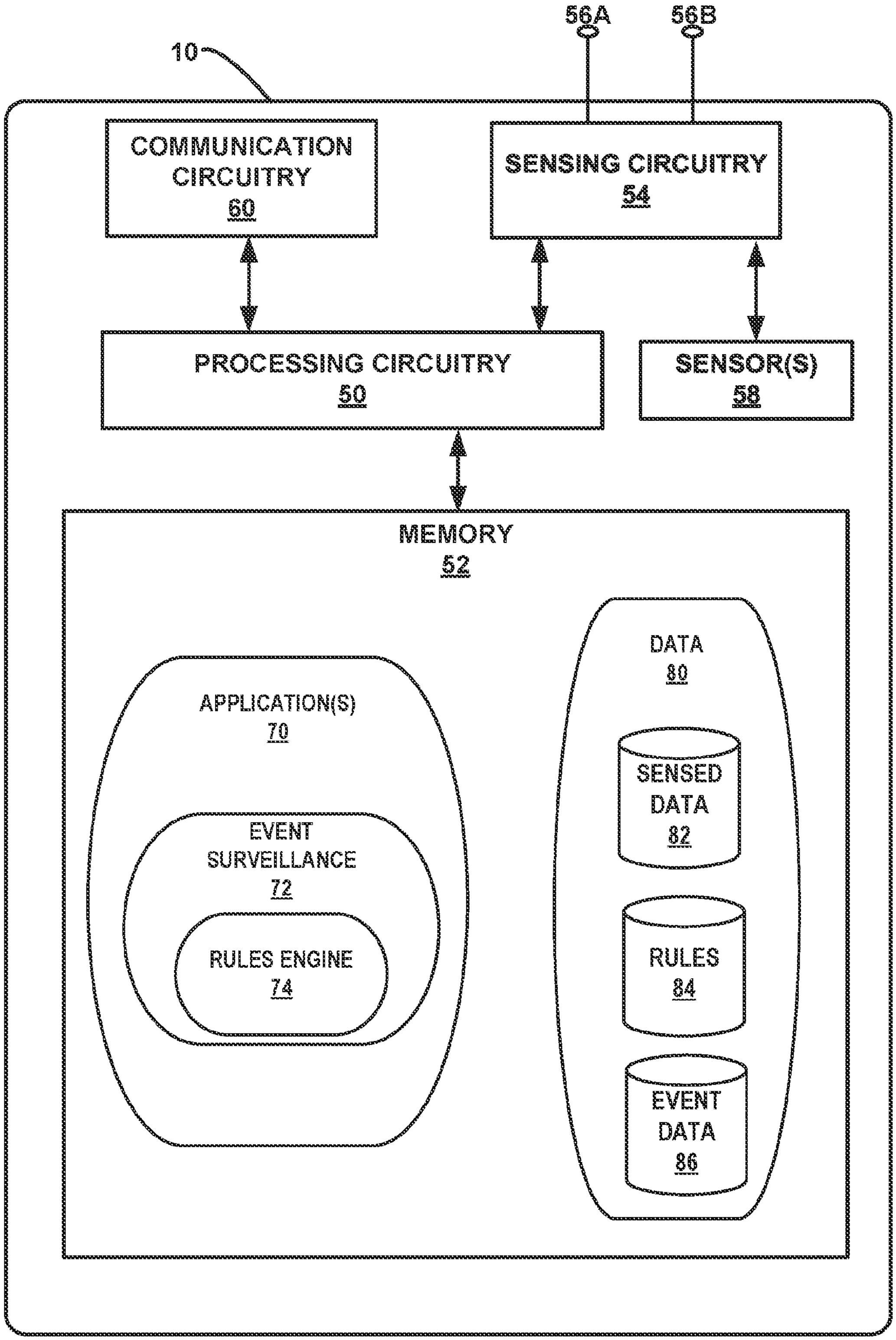
FIG. 2 is a block diagram illustrating an example configuration of a patient sensing device that operates in accordance with one or more techniques of the present disclosure.

FIG. 2 is a block diagram illustrating an example configuration of IMD 10 of FIG. 1. As shown in FIG. 2, IMD 10 includes processing circuitry 50, memory 52, sensing circuitry 54 coupled to electrodes 56A and 56B (hereinafter, "electrodes 56") and one or more sensor(s) 58, and communication circuitry 60.

Processing circuitry 50 may include fixed function circuitry and/or programmable processing circuitry. Processing circuitry 50 may include any one or more of a microprocessor, a controller, a graphics processing unit (GPU), a tensor processing unit (TPU), a digital signal processor (DSP), an application specific integrated circuit (ASIC), a field-programmable gate array (FPGA), or equivalent discrete or analog logic circuitry. In some examples, processing circuitry 50 may include multiple components, such as any combination of one or more microprocessors, one or more controllers, one or more GPUs, one or more TPUs, one or more DSPs, one or more ASICs, or one or more FPGAs, as well as other discrete or integrated logic circuitry. The functions attributed to processing circuitry 50 herein may be embodied as software, firmware, hardware, or any combination thereof. In some examples, memory 53 includes computer-readable instructions that, when executed by processing circuitry 50, cause IMD 10 and processing circuitry 50 to perform various functions attributed herein to IMD 10 and processing circuitry 50. Memory 53 may include any volatile, non-volatile, magnetic, optical, or electrical media, such as a random-access memory (RAM), read-only memory (ROM), non-volatile RAM (NVRAM), electrically-erasable programmable ROM (EEPROM), flash memory, or any other digital media.

Sensing circuitry 54 may monitor signals from electrodes 56 in order to, for example, monitor electrical activity of a heart of patient 4 and produce ECG data for patient 4. In some examples, processing circuitry 50 may identify features of the sensed ECG, such as heart rate, heart rate variability, intra-beat intervals, and/or ECG morphologic features, to detect an episode of cardiac arrhythmia of patient 4. Processing circuitry 50 may store the digitized ECG and features of the ECG used to detect the arrhythmia episode in memory 52 as episode data for the detected arrhythmia episode.

In some examples, sensing circuitry 54 measures impedance, e.g., of tissue proximate to IMD 10, via electrodes 56. The measured impedance may vary based on respiration and a degree of perfusion or edema. Processing circuitry 50 may determine physiological data relating to respiration, perfusion, and/or edema based on the measured impedance.

In some examples, IMD 10 includes sensing circuitry 58, such as one or more accelerometers, microphones, optical sensors, temperature sensors, and/or pressure sensors. In some examples, sensing circuitry 54 may include one or more filters and amplifiers for filtering and amplifying signals received from one or more of electrodes 56 and/or sensors 58. In some examples, sensing circuitry 54 and/or processing circuitry 50 may include a rectifier, filter and/or amplifier, a sense amplifier, comparator, and/or analog-to-digital converter. Processing circuitry 50 may determine physiological data, e.g., values of physiological parameters of patient 4, based on signals from sensors 58, which may be stored in memory 52.

Memory 52 may store applications 70 executable by processing circuitry 50, and data 80. Applications 70 may include an acute health event surveillance application 72. Processing circuitry 50 may execute event surveillance application 72 to detect an acute health event of patient 4 based on combination of one or more of the types of physiological data described herein, which may be stored as sensed data 82. In some examples, sensed data 82 may additionally include data sensed by other devices. e.g., computing device(s) 12, and received via communication circuitry 60. Event surveillance application 72 may be configured with a rules engine 74. Rules engine 74 may apply rules 84 to sensed data 82. Rules 84 may include one or more models, algorithms, decision trees, and/or thresholds. In some cases, rules 84 may be developed based on machine learning.

As examples, event surveillance application 72 may detect a cardiac arrest, a ventricular fibrillation, a ventricular tachycardia, a cardiac pause of asystole, pulseless electrical activity (PEA), or a myocardial infarction based on an ECG and/or other physiological data indicating the electrical or mechanical activity of heart 6 of patient 4 (FIG. 1). In some examples, event surveillance application 72 may detect stroke based on such cardiac activity data. In some examples, sensing circuitry 54 may detect brain activity data, e.g., an electroencephalogram (EEG) via electrodes 56, and event surveillance application 72 may detect stroke or a seizure based on the brain activity alone, or in combination with cardiac activity data or other physiological data. In some examples, event surveillance application 72 detects whether the patient has fallen based on data from an accelerometer alone, or in combination with other physiological data. When event surveillance application 72 detects an acute health event, event surveillance application 72 may store the sensed data 82 that lead to the detection (and in some cases a window of data preceding and/or following the detection) as event data 86.

In some examples, in response to detection of an acute health event, processing circuitry 50 transmits, via communication circuitry 60, event data 86 for the event to computing device(s) 12 (FIG. 1). This transmission may be included in a message indicating the acute health event, as described herein. In some examples, transmission of the message may occur on an ad hoc basis and as quickly as possible. Communication circuitry 60 may include any suitable hardware, firmware, software, or any combination thereof for wirelessly communicating with another device, such as computing devices 12 and/or IoT devices 30. In response to receiving the message, computing device(s) 12 may attempt to elicit a response from patient 4 as discussed above with respect to FIG. 1.

Figure 3:
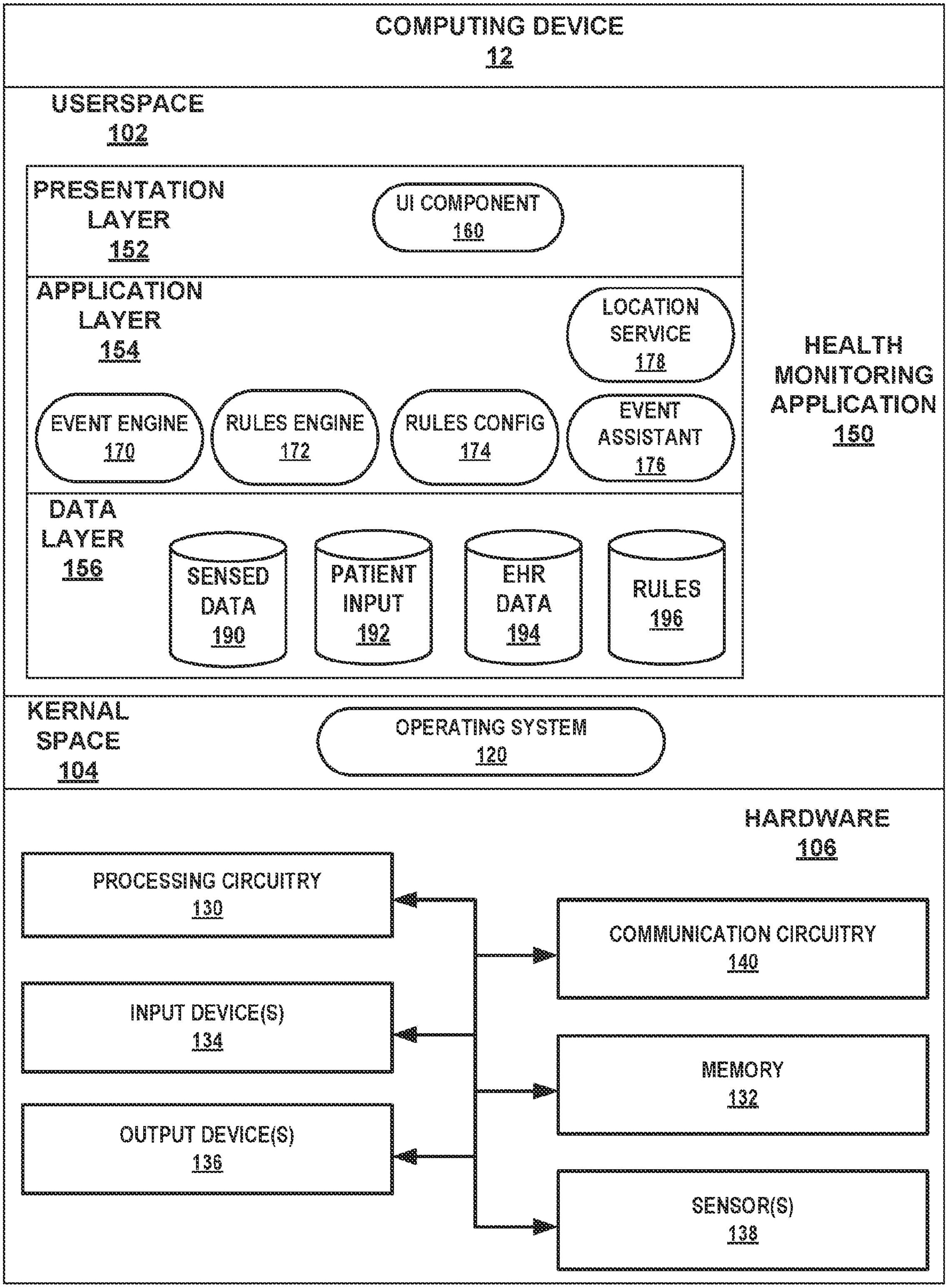
FIG. 3 is block diagram illustrating an example configuration of a computing device that operates in accordance with one or more techniques of the present disclosure.

FIG. 3 is a block diagram illustrating an example configuration of a computing device 12 of patient 4, which may correspond to either (or both operating in coordination) of computing devices 12A and 12B illustrated in FIG. 1. In some examples, computing device 12 takes the form of a smartphone, a laptop, a tablet computer, a personal digital assistant (PDA), a smartwatch or other wearable computing device. In some examples, IoT devices 30, drone 46, and robot 48 may be configured similarly to the configuration of computing device 12 illustrated in FIG. 3.

As shown in the example of FIG. 3, computing device 12 may be logically divided into user space 102, kernel space 104, and hardware 106. Hardware 106 may include one or more hardware components that provide an operating environment for components executing in user space 102 and kernel space 104. User space 102 and kernel space 104 may represent different sections or segmentations of memory, where kernel space 104 provides higher privileges to processes and threads than user space 102. For instance, kernel space 104 may include operating system 120, which operates with higher privileges than components executing in user space 102.

As shown in FIG. 3, hardware 106 includes processing circuitry 130, memory 132, one or more input devices 134, one or more output devices 136, sensing circuitry 138, and communication circuitry 140. Although shown in FIG. 3 as a stand-alone device for purposes of example, computing device 12 may be any component or system that includes processing circuitry or other suitable computing environment for executing software instructions and, for example, need not necessarily include one or more elements shown in FIG. 3.

Processing circuitry 130 is configured to implement functionality and/or process instructions for execution within computing device 12. For example, processing circuitry 130 may be configured to receive and process instructions stored in memory 132 that provide functionality of components included in kernel space 104 and user space 102 to perform one or more operations in accordance with techniques of this disclosure. Examples of processing circuitry 130 may include, any one or more microprocessors, controllers, GPUs, TPUs, DSPs, ASICs, FPGAs, or equivalent discrete or integrated logic circuitry.

Memory 132 may be configured to store information within computing device 12, for processing during operation of computing device 12. Memory 132, in some examples, is described as a computer-readable storage medium. In some examples, memory 132 includes a temporary memory or a volatile memory. Examples of volatile memories include random access memories (RAM), dynamic random-access memories (DRAM), static random-access memories (SRAM), and other forms of volatile memories known in the art. Memory 132, in some examples, also includes one or more memories configured for long-term storage of information, e.g., including non-volatile storage elements. Examples of such non-volatile storage elements include magnetic hard discs, optical discs, floppy discs, flash memories, or forms of electrically programmable memories (EPROM) or electrically erasable and programmable (EEPROM) memories.

One or more input devices 134 of computing device 12 may receive input, e.g., from patient 4 or another user. Examples of input are tactile, audio, kinetic, and optical input. Input devices 134 may include, as examples, a mouse, keyboard, voice responsive system, camera, buttons, control pad, microphone, presence-sensitive or touch-sensitive component (e.g., screen), or any other device for detecting input from a user or a machine.

One or more output devices 136 of computing device 12 may generate output, e.g., to patient 4 or another user. Examples of output are tactile, audio, and visual output. Output devices 136 of computing device 12 may include a presence-sensitive screen, sound card, video graphics adapter card, speaker, cathode ray tube (CRT) monitor, liquid crystal display (LCD), light emitting diodes (LEDs), or any type of device for generating tactile, audio, and/or visual output.

Sensing circuitry 138 of computing device 12 may sense physiological parameters or signals of patient 4. Sensor(s) 138 may include electrodes, 3-axis accelerometers, an optical sensor, impedance sensors, temperature sensors, pressure sensors, heart sounds sensors, and other sensors, and sensing circuitry (e.g., including an ADC), similar to those described above with respect to IMD 10 and FIG. 2.

Communication circuitry 140 of computing device 12 may communicate with other devices by transmitting and receiving data. Communication circuitry 140 may include a network interface card, such as an Ethernet card, an optical transceiver, a radio frequency transceiver, or any other type of device that can send and receive information. For example, communication circuitry 140 may include a radio transceiver configured for communication according to standards or protocols, such as 3G, 4G, 5G, WiFi (e.g., 802.11 or 802.15 ZigBee), Bluetooth®, or Bluetooth® Low Energy (BLE).

As shown in FIG. 3, health monitoring application 150 executes in user space 102 of computing device 12. Health monitoring application 150 may be logically divided into presentation layer 152, application layer 154, and data layer 156. Presentation layer 152 may include a user interface (UI) component 160, which generates and renders user interfaces of health monitoring application 150.

Application layer 154 may include, but is not limited to, an event engine 170, rules engine 172, rules configuration component 174, event assistant 176, and location service 178. Event engine 170 may be responsive to receipt of an alert transmission from IMD 10 indicating that IMD 10 detected an acute health event. Event engine 170 may control performance of any of the operations in response to detection of an acute health event ascribed herein to computing device 12, such as activating an alarm, transmitting alert messages to HMS 22, controlling IoT devices 30, and analyzing data to confirm or override the detection of the acute health event by IMD 10.

Rules engine 172 analyzes sensed data 190, and in some examples, patient input 192 and/or EHR data 194, to determine whether there is a sufficient likelihood that patient 4 is experiencing the acute health event detected by IMD 10 or to verify that patient 4 has experienced the acute health event detected by IMD 10. Sensed data 190 may include data received from IMD 10 as part of the alert transmission, additional data transmitted from IMD 10, e.g., in "real-time," and physiological parameters and other data related to the condition of patient 4 collected by computing device(s) 12, IoT devices 30, drone 46, and/or robot 48. Rules engine 172 may determine whether the physiological parameters meet predefined criteria to verify the acute health event. As examples sensed data 190 from computing device(s) 12 may include one or more of: activity levels, walking/running distance, resting energy, active energy, exercise minutes, quantifications of standing, body mass, body mass index, heart rate, low, high, and/or irregular heart rate events, heart rate variability, walking heart rate, heart beat series, digitized ECG, blood oxygen saturation, blood pressure (systolic and/or diastolic), respiratory rate, maximum volume of oxygen, blood glucose, peripheral perfusion, and sleep patterns.

Patient input 192 may include responses to queries posed by health monitoring application 150 regarding the condition of patient 4, input by patient 4 or another user, such as bystander 26. The queries and responses may occur responsive to the detection of the event by IMD 10, and/or may have occurred prior to the detection, e.g., as part long-term monitoring of the health of patient 4. User recorded health data of patient input 192 may include one or more of: exercise and activity data, sleep data, symptom data, medical history data, quality of life data, nutrition data, medication taking or compliance data, allergy data, demographic data, weight, and height. EHR data 194 may include any of the information regarding the historical condition or treatments of patient 4 described above. EHR data 194 may relate to history of cardiac arrest, tachyarrhythmia, myocardial infarction, stroke, seizure, chronic obstructive pulmonary disease (COPD), renal dysfunction, or hypertension, history of procedures, such as ablation or cardioversion, and healthcare utilization. EHR data 194 may also include demographic and other information of patient 4, such as age, gender, height, weight, and BMI.

Rules engine 172 may apply rules 196 to the data. Rules 196 may include one or more models, algorithms, decision trees, and/or thresholds. In some cases, rules 196 may be developed based on machine learning. In some examples, rules 196 and the operation of rules engine 172 may provide a more complex analysis of the sensed data received from IMD 10, than is provided by rules engine 74 and rules 84. In some examples, rules 196 include one or more models developed by machine learning, and rules engine 172 applies feature vectors derived from the data to the model(s). For example, rules engine 172 may apply rules 196 to determine whether the physiological parameters captured by IMD 10 and the verification device or system meet predefined criteria to verify the acute health event.

Rules configuration component 174 may be configured to modify rules 196 (and in some examples rules 84) based on feedback indicating whether the detections and confirmations of acute health events by IMD 10 and computing device 12 were accurate. The feedback may be received from patient 4, or from care providers 40 and/or EHR 24 via HMS 22. In some examples, rules configuration component 174 may utilize the data sets from true and false detections and confirmations for supervised machine learning to further train models included as part of rules 196.

As discussed above, event assistant 176 may provide a conversational interface or tactile interface for patient 4 and/or bystander 26 to exchange information with computing device 12. Event assistant 176 may query the user regarding the condition of patient 4 in response to receiving the alert message from IMD 10. Responses from the user may be included as patient input 192. Event assistant 176 may use natural language processing and context data to interpret utterances by the user. In some examples, in addition to receiving responses to queries posed by the assistant, event assistant 176 may be configured to respond to queries posed by the user. In some examples, event assistant 176 may provide directions or instructions to and respond to queries regarding treatment of patient 4 from patient 4 or bystander 26.

Location service 178 may determine the location of computing device 12 and, thereby, the presumed location of patient 4. Location service 178 may use global position system (GPS) data, multilateration, and/or any other known techniques for locating computing devices. In some examples, location service 178 may utilize data from other devices to determine the location of patient 4, such as IoT devices 30, drone 46, or robot 48. For example, data from a camera, a radar system, a sonar system, or a lidar system may be used to determine where in environment 28 (FIG. 1) patient 4 is located. In some examples, location service 178 may track where patient 4 is during different times of the day and use the most frequent location at the time of the day that the indication of the acute medical event was sensed as a starting position to determine the location of patient 4. For example, location service 178 may employ one or more of the devices, such as IoT devices 30, drone 46, and/or robot 48, to check to see if patient 4 is located at the most frequent location for that time of day.

Figure 4:
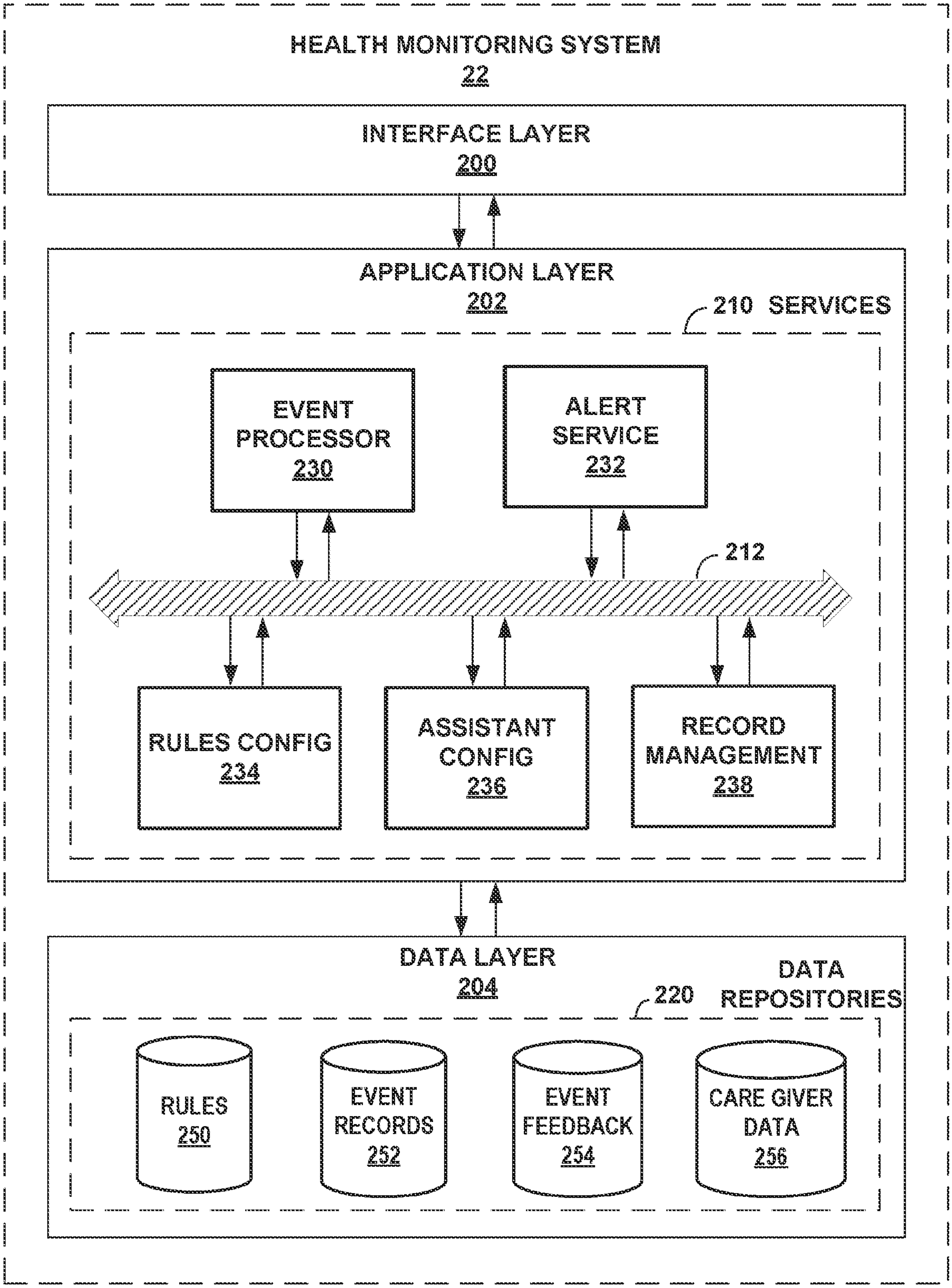
FIG. 4 is a block diagram illustrating an example configuration of a health monitoring system that operates in accordance with one or more techniques of the present disclosure.

FIG. 4 is a block diagram illustrating an operating perspective of HMS 22. HMS 22 may be implemented in a computing system 20, which may include hardware components such as those of computing device 12, embodied in one or more physical devices. FIG. 4 provides an operating perspective of HMS 22 when hosted as a cloud-based platform. In the example of FIG. 4, components of HMS 22 are arranged according to multiple logical layers that implement the techniques of this disclosure. Each layer may be implemented by one or more modules comprised of hardware, software, or a combination of hardware and software.

Computing devices, such as computing devices 12, IoT devices 30, computing devices 38, computing device 42, drone 46, and/or robot 48, may operate as clients that communicate with HMS 22 via interface layer 200. The computing devices typically execute client software applications, such as desktop application, mobile application, and/or web applications. Interface layer 200 represents a set of application programming interfaces (API) or protocol interfaces presented and supported by HMS 22 for the client software applications. Interface layer 200 may be implemented with one or more web servers.

As shown in FIG. 4, HMS 22 also includes an application layer 202 that represents a collection of services 210 for implementing the functionality ascribed to HMS herein. Application layer 202 receives information from client applications. e.g., an alert of an acute health event from one or more computing device 12 and/or IoT device 30, and further processes the information according to one or more of the services 210 to respond to the information. Application layer 202 may be implemented as one or more discrete software services 210 executing on one or more application servers, e.g., physical or virtual machines. That is, the application servers provide runtime environments for execution of services 210. In some examples, the functionality interface layer 200 as described above and the functionality of application layer 202 may be implemented at the same server. Services 210 may communicate via a logical service bus 212. Service bus 212 generally represents a logical interconnections or set of interfaces that allows different services 210 to send messages to other services, such as by a publish/subscription communication model.

Data layer 204 of HMS 22 provides persistence for information in PPEMS 6 using one or more data repositories 220. A data repository 220, generally, may be any data structure or software that stores and/or manages data. Examples of data repositories 220 include but are not limited to relational databases, multi-dimensional databases, maps, and hash tables, to name only a few examples.

As shown in FIG. 4, each of services 230-238 is implemented in a modular form within HMS 22. Although shown as separate modules for each service, in some examples the functionality of two or more services may be combined into a single module or component. Each of services 230-238 may be implemented in software, hardware, or a combination of hardware and software. Moreover, services 230-238 may be implemented as standalone devices, separate virtual machines or containers, processes, threads or software instructions generally for execution on one or more physical processors.

Event processor service 230 may be responsive to receipt of an alert transmission from computing device(s) 12 and/or IoT device(s) 30 indicating that IMD 10 detected an acute health event of patient and, in some examples, that the transmitting device confirmed or verified the detection. Event processor service 230 may initiate performance of any of the operations in response to detection of an acute health event ascribed herein to HMS 22, such as communicating with patient 4, bystander 26, and care providers 40, activating the verification device or system (e.g., any of IoT devices 30, computing device(s) 12, drone 46, or robot 48) and, in some cases, analyzing data to confirm or override the detection of the acute health event by IMD 10. In some examples, rather than actually verifying the acute health event, the verification device or system may transmit the sensed physiological parameters to HMS 22 and HMS 22 may verify the acute health event.

Record management service 238 may store the patient data included in a received alert message within event records 252. Alert service 232 may package some or all of the data from the event record, in some cases with additional information as described herein, into one more alert messages for transmission to bystander 26 and/or care providers 40. Care provider data 256 may store data used by alert service 232 to identify to whom to send alerts based on locations of potential bystanders 26 and care providers 40 relative to a location of patient 4 and/or applicability of the care provided by care providers 40 to the acute health event experienced by patient 4.

In examples in which HMS 22 performs an analysis to confirm, verify, or override the detection of the acute health event by IMD 10, event processor service 230 may apply one or more rules 250 to the data received in the alert message. e.g., to feature vectors derived by event processor service 230 from the data. Rules 250 may include one or more models, algorithms, decision trees, and/or thresholds, which may be developed by rules configuration service 234 based on machine learning. Example machine learning techniques that may be employed to generate rules 250 can include various learning styles, such as supervised learning, unsupervised learning, and semi-supervised learning. Example types of algorithms include Bayesian algorithms, Clustering algorithms, decision-tree algorithms, regularization algorithms, regression algorithms, instance-based algorithms, artificial neural network algorithms, deep learning algorithms, dimensionality reduction algorithms and the like. Various examples of specific algorithms include Bayesian Linear Regression, Boosted Decision Tree Regression, and Neural Network Regression, Back Propagation Neural Networks. Convolution Neural Networks (CNN), Long Short Term Networks (LSTM), the Apriori algorithm, K-Means Clustering, k-Nearest Neighbour (kNN), Learning Vector Quantization (LVQ). Self-Organizing Map (SOM), Locally Weighted Learning (LWL), Ridge Regression, Least Absolute Shrinkage and Selection Operator (LASSO), Elastic Net, and Least-Angle Regression (LARS), Principal Component Analysis (PCA) and Principal Component Regression (PCR).

In some examples, in addition to rules used by HMS 22 to confirm acute health event detection. (or in examples in which HMS 22 does not confirm event detection) rules 250 maintained by HMS 22 may include rules 196 utilized by computing devices 12 and rules 84 used by IMD 10. In such examples, rules configuration service 234 may be configured to develop and maintain rules 196 and rules 84. Rules configuration service 234 may be configured to modify these rules based on event feedback data 254 that indicates whether the detections and confirmations of acute health events by IMD 10, computing device 12, and/or HMS 22 were accurate. Event feedback data 254 may be received from patient 4. e.g., via computing device(s) 12, or from care providers 40 and/or EHR 24. In some examples, rules configuration service 234 may utilize event records from true and false detections (as indicated by event feedback data 254) and confirmations for supervised machine learning to further train models included as part of rules 250.

As illustrated in the example of FIG. 4, services 210 may also include an assistant configuration service 236 for configuring and interacting with event assistant 176 implemented in computing device 12 or other computing devices.

Figure 5:
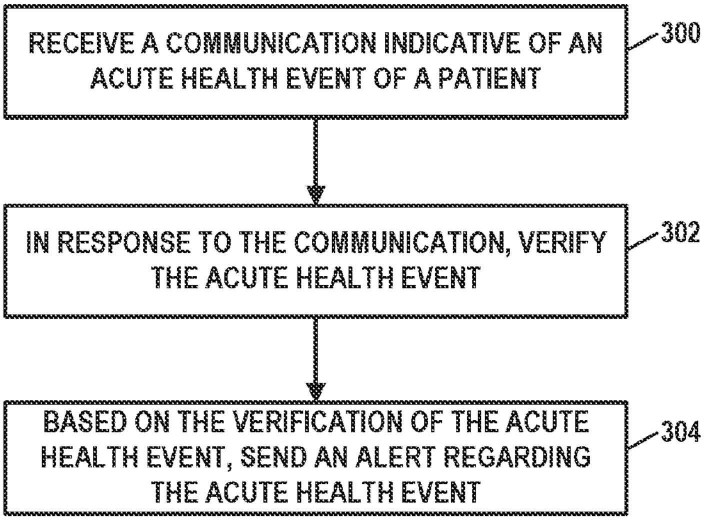
FIG. 5 is a flow diagram illustrating verification techniques according to the present disclosure.

FIG. 5 is a flow diagram illustrating verification techniques according to the present disclosure. Computing device 12A or computing device 12B may receive a communication indicative of an acute health event of patient 4 (300). For example, IMD 10 may monitor physiological parameters of patient 4 and detect an indication of an acute health event of patient 4. Computing device 12A or computing device 12B may receive a communication including an indication of the acute health event from IMD 10.

In response to the communication, computing device 12A or computing device 12B may verify the acute health event (302). For example, computing device 12A or computing device 12B may communicatively connect to any of IoT device(s) 30A-30D, drone 46, and/or robot 48. Computing device 12A or computing device 12B may instruct any of IoT device(s) 30A-30D, drone 46, and/or robot 48 to collect information relating to physiological parameters of patient 4. Computing device 12A or computing device 12B may receive information from at least one of the IoT device, drone, or robot (e.g., the instructed devices) indicative of a verification of the acute health event (e.g., physiological parameters of patient 4). Computing device 12A or computing device 12B may process the information and based on the processed information, confirm the acute health event.

Based on the verification of the acute health event, computing device 12A or computing device 12B may send an alert regarding the acute health event (306). For example, computing device 12A or computing device 12B may send the alert shortly after the verification of the acute health event so as to be close enough to the occurrence of the acute health event to provide an opportunity for successful life-saving measures to be taken with regard to patient 4. In some examples, the alert includes at least one of a telephone call, a short message service message, an email, a web alert, a security system alert, a social media alert, an audible alert, a visual alert, or a smart device push notification.

In some examples, the received communication is from an implantable medical device. In some examples, computing device 12A or computing device 12B may prompt patient 4 to provide a response. In some examples, the computing device includes a smartphone, a wearable device, or an IoT device. In some examples, the response is at least one of an audible response indicative of the patient not having experienced the acute health event or a tactile response indicative of the patient not having experienced the acute health event. For example, the audible response may be a voice response or other noise response (e.g., a clap). For example, the tactile response may be a button push, fingerprint swipe, touch pad entry, or the like.

In some examples, computing device 12A or computing device 12B may receive information from at least one of IoT device 30A, drone 46, or robot 48 indicative of a verification of the acute health event. In some examples, the received information is from IoT device 30A and IoT device 30A comprises a video camera, an infrared camera, a thermal camera, a radar system, a sonar system, a lidar system, a bed sensor, a smart speaker, or a smart television.

In some examples, based on the verification of the acute health event, computing device 12A or computing device 12B transmit a communication to robot 48 instructing robot 48 to medically intervene with patient 4. In some examples, verifying the acute health event includes determining physiological parameters of patient 4. For example, computing device 12A or computing device 12B may receive information indicative of physiological parameters of patient 4 from any of IoT devices 30, drone 46, or robot 48 and may determine the physiological parameters based on the information. In some examples, the physiological parameters of the patient include at least one of pulse rate, blood perfusion, breathing rate, breathing intensity, posture, facial features, color of a face, or an electrocardiogram. In some examples, verifying the acute health event includes determining whether the physiological parameters of the patient meet predefined criteria. For example, computing device 12A or computing device 12B may determine whether physiological parameters meet predefined criteria.

In some examples, computing device 12A or computing device 12B may determine a location of patient 4. In some examples, computing device 12A or computing device 12B may open smart locks.

In some examples, the alert includes data indicative of physiological parameters of the patient. In some examples, the acute health event includes at least one of sudden cardiac arrest, stroke, acute myocardial infarction, epilepsy, fall, respiratory failure, or anaphylactic shock.

Significant actions may occur within a short period of time when a medical device, such as IMD 10, detects a cardiac event, such as a ventricular arrhythmia. For example, an implantable cardioverter defibrillator (ICD) or a wearable cardioverter defibrillator (WCD) may deliver a shock to patient 4 to terminate the arrythmia, or may send an alert to an EMS, to bystander 26, or to robot 48 to deliver medical treatment (e.g., CPR, a shock using AED 44, epinephrine, or other treatment) to patient 4. Shocks may be painful to patient 4 and may have adverse effects (e.g., on the myocardium of patient 4). Other devices, such as ICMs or external devices (e.g., wearable devices, such as a smart watch or fitness watch, an event recorder, a Holter monitor, or other device configured to monitor cardiac activity) may also monitor for ventricular arrhythmias and may send an alert to EMS, to bystander 26, or to robot 48 to deliver medical treatment (e.g., CPR, a shock using AED 44, epinephrine, or other treatment) to patient 4. However, in many instances, such treatment is not necessary as research shows that many of the ventricular arrythmia episodes self-terminate within a reasonable amount of time.

Figure 6:
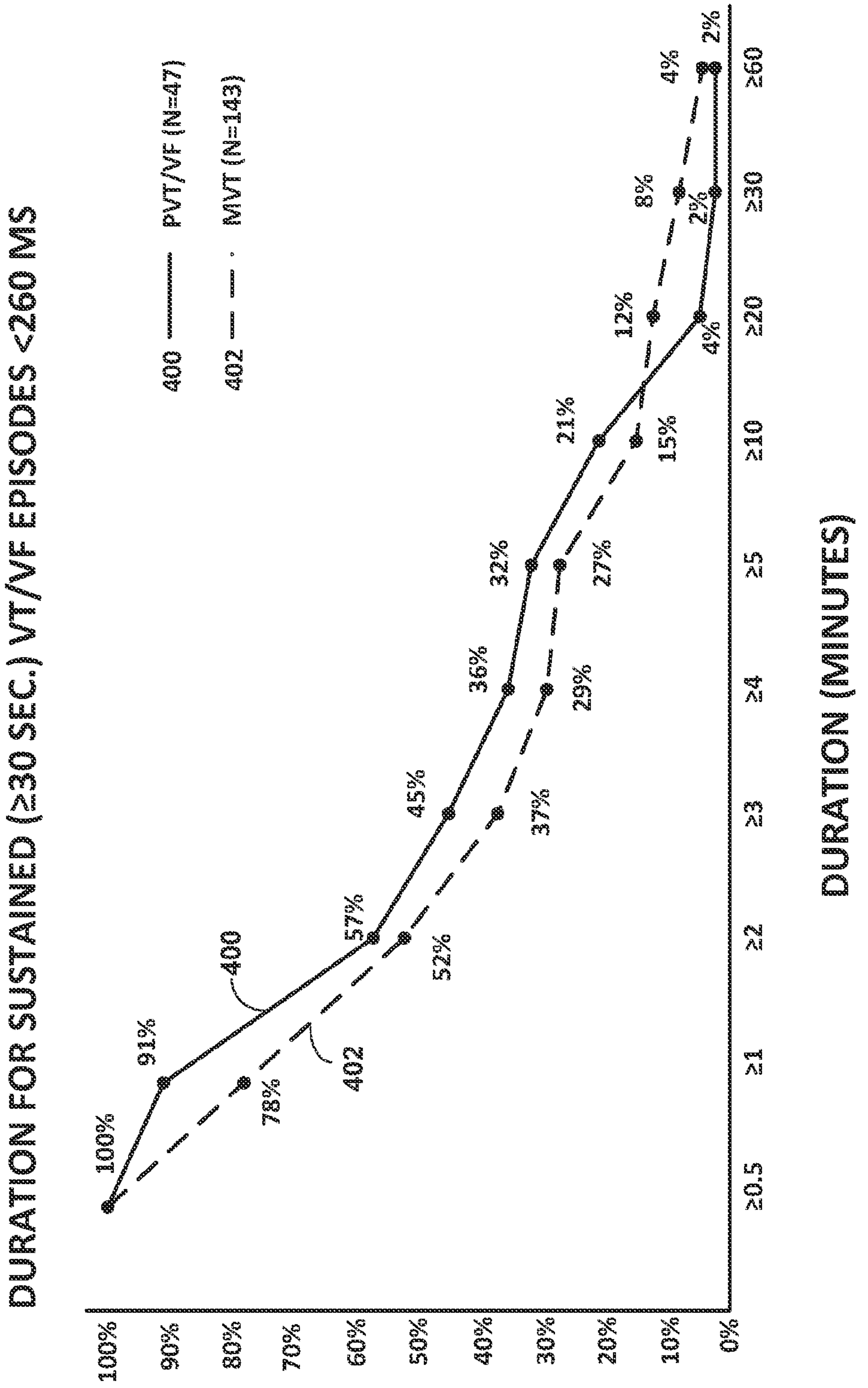
FIG. 6 is a graphical diagram illustrating results of a study on self-terminating ventricular arrythmias.

FIG. 6 is a graphical diagram illustrating results of a study on self-terminating ventricular arrythmias. In this study, data was collected from ICMs implanted within cardiac patients. The horizontal or x axis indicates the duration in minutes of an event. The vertical or y axis indicates the percentage of clinically sustained events that were still ongoing. Line 400 shows pulseless VT or VF (PVT/VF) and line 402 shows monomorphic VT episodes (MVT). The data of FIG. 6 shows that for VT or VF episodes that are clinically sustained (e.g., which last for at least 30 seconds) nearly half self-terminate within 2 minutes. For example, line 400 shows that 43% of pulseless VT or VF episodes self-terminated within 2 minutes. Line 402 shows that 48% of MVT episodes self-terminated within 2 minutes.

In a publication regarding another study, Valentina Kutyifa et al., "Use of the Wearable Cardioverter Defibrillator in High-Risk Cardiac Patients: Data From the Prospective Registry of Patients Using the Wearable Cardioverter Defibrillator (WEARIT-II Registry)," Aug. 27, 2015, the authors found a similar outcome. This study found that a majority of the sustained VT or VF episodes did not require a shock. In the study, a total number of 120 sustained VT or VF events occurred in 41 patients, corresponding to a rate of 22 sustained episodes per 100 patient-years. In this study, the patients had the ability to delay therapy by pressing a response button. Most of the sustained VT episodes were not treated by the WCD because the patient used the response button to delay therapy, and, subsequently, the VT episodes self-terminated. In 90 of the sustained VT events in the 22 patients, therapy was not delivered. Whereas in 30 events in the 22 patients, shock therapy was delivered due to hemodynamic instability (corresponding to 5 events per 100 patient-years).

While data from these two studies shows that many of the true VT or VF episodes self-terminate in a short time span, many clinicians are reluctant to wait longer (e.g., to program IMD 10 to wait longer) to administer shocks. Accurate prediction of which VT or VF episodes may dramatically reduce the number of unnecessary ICD. WCD, or AED shocks being delivered to patients.

Therefore, it may be desirable to accurately predict which ventricular arrythmia episodes may self-terminate so as to avoid unnecessary treatment and/or use of EMS resources. For example, IMD 10, computing devices 12. IoT devices 30, or HMS 22 may utilize one or more algorithms, such as a machine learning model, or other artificial intelligence, to assess the early stage of a VT or VF episode and/or the prior history of patient 4 (e.g., from data collected from IMD 10, computing devices 12, IoT devices 30, drone 46, robot 48, HMS 22, and/or EHR 24) to predict if the ventricular arrhythmia will self-terminate, and therefore, not require intervention. For example, if processing circuitry of system 2 were to be able to determine which episodes would self-terminate and which would not self-terminate, system 2 may selectively only treat, send alerts, or dispatch robot 48 to treat patient 4 when the episode is determined to be a sustained episode that may not self-terminate saving resources and protecting patient 4 against unnecessary treatment.

For example, based on the application of rules, e.g., a machine learning model or other artificial intelligence algorithm, decision trees, and/or thresholds, system 2 may determine whether a cardiac event, such as ventricular arrythmia, may be likely to self-terminate or be unlikely to self-terminate. For example, a machine learning model may analyze ECG data, bio markers, activity level, posture, heart rate variability, other physiologic data collected by IMD 10, computing devices 12, IoT devices 30, and/or other devices, history of self-termination status of cardiac events, and/or historical information about the patient (e.g., prior heart rhythms, demographical data, etc., which may be located in EHR 24 or in HMS 22) to predict which VT or VF episodes will self-terminate and which ones will continue to be sustained and require therapy and EMS resources.

Figure 7:
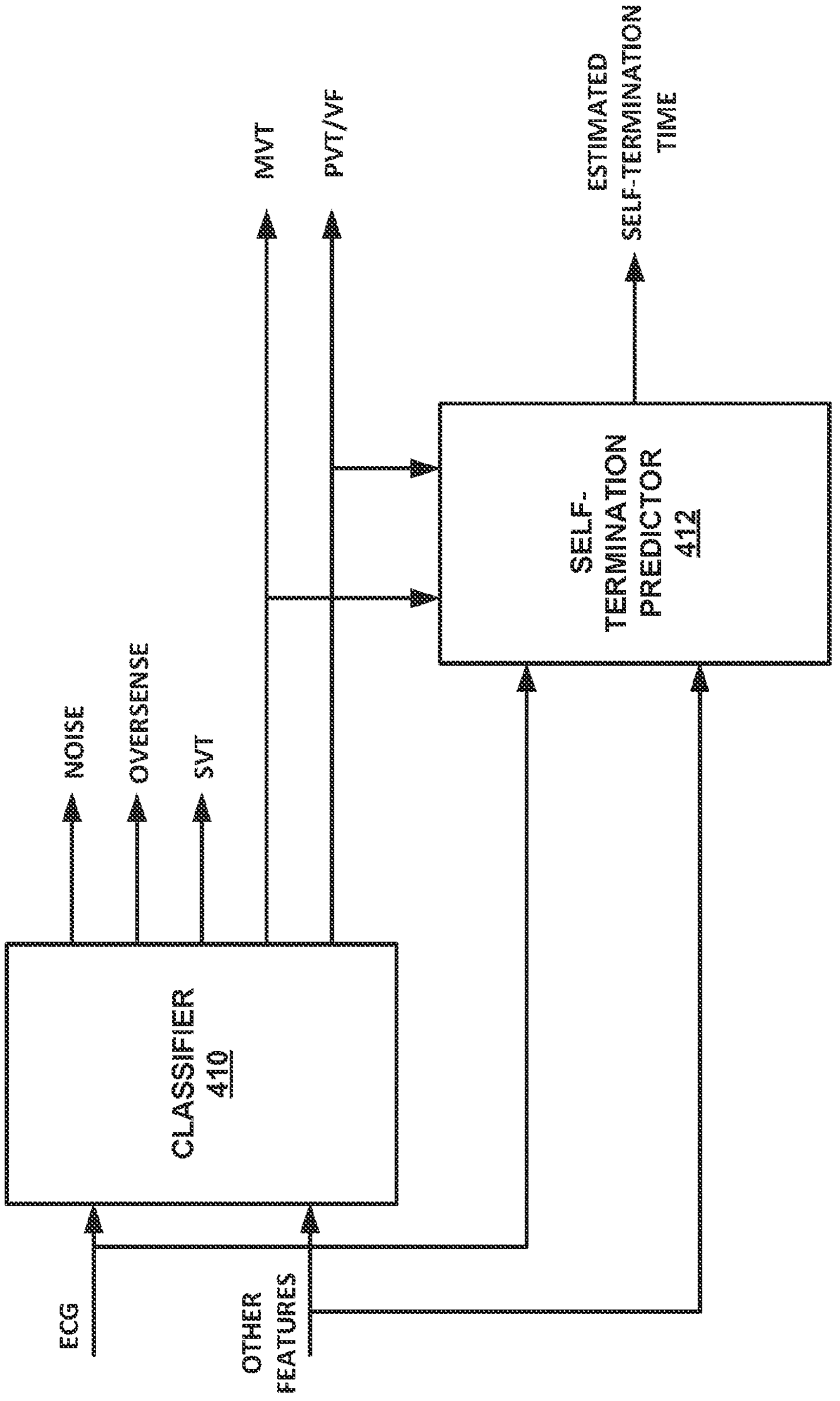
FIG. 7 is a block diagram illustrating an example of the use of two artificial intelligence or machine learning models in the determination of whether a given VT or VF episode may self-terminate.

FIG. 7 is a block diagram illustrating an example of the use of two artificial intelligence or machine learning models in the determination of whether a given VT or VF episode may self-terminate. In some examples, a classifier 410 may classify a cardiac event, such as to verify that the cardiac event is a true cardiac event. For example, classifier 410 may be a 5-class artificial intelligence classifier which may classify the event as noise, over sensing, an SVT event, an MVT event, or a PVT or VF event. This information and/or information used by classifier 410 may be passed on to a secondary model, e.g., self-termination predictor 412, which may predict a time to self-termination. Self-termination predictor 412 may determine a cutoff time, which may be different for different patients (e.g., based on clinical history or based on the type of episode). For example, system 2 may wait longer (2-5 minutes) for an MVT which is hemodynamically stable to self-terminate prior to taking action, such as shocking or sending an alert, while only waiting 30 seconds in case of VF which is hemodynamically unstable or in cases where patient 4 has fallen down.

In some examples, self-termination predictor 412 may continuously ingest data (e.g., streaming ECG data and/or other sensed physiological parameters) over time and use data from history, e.g., prior to onset of the event or clinical history, to update the estimated time to self-termination. Self-termination predictor 412 may have many input physiological parameters, and may use the raw ECG data, as well as derived features using continuous wavelet transforms, short time Fourier transform, autocorrelation/cross-correlations, etc., to track ECG morphological changes or physiological parameter morphological changes over time and update the estimated self-termination time periodically (e.g., every 10 seconds). In some examples, self-termination predication model 412 is a deep learning network that may use LSTM or other forms of recurrent neural network (RNN) architecture, as well as CNN, that is fed into a fully connected layer which then feeds into a regression layer to estimate the self-termination time.

Figure 8:
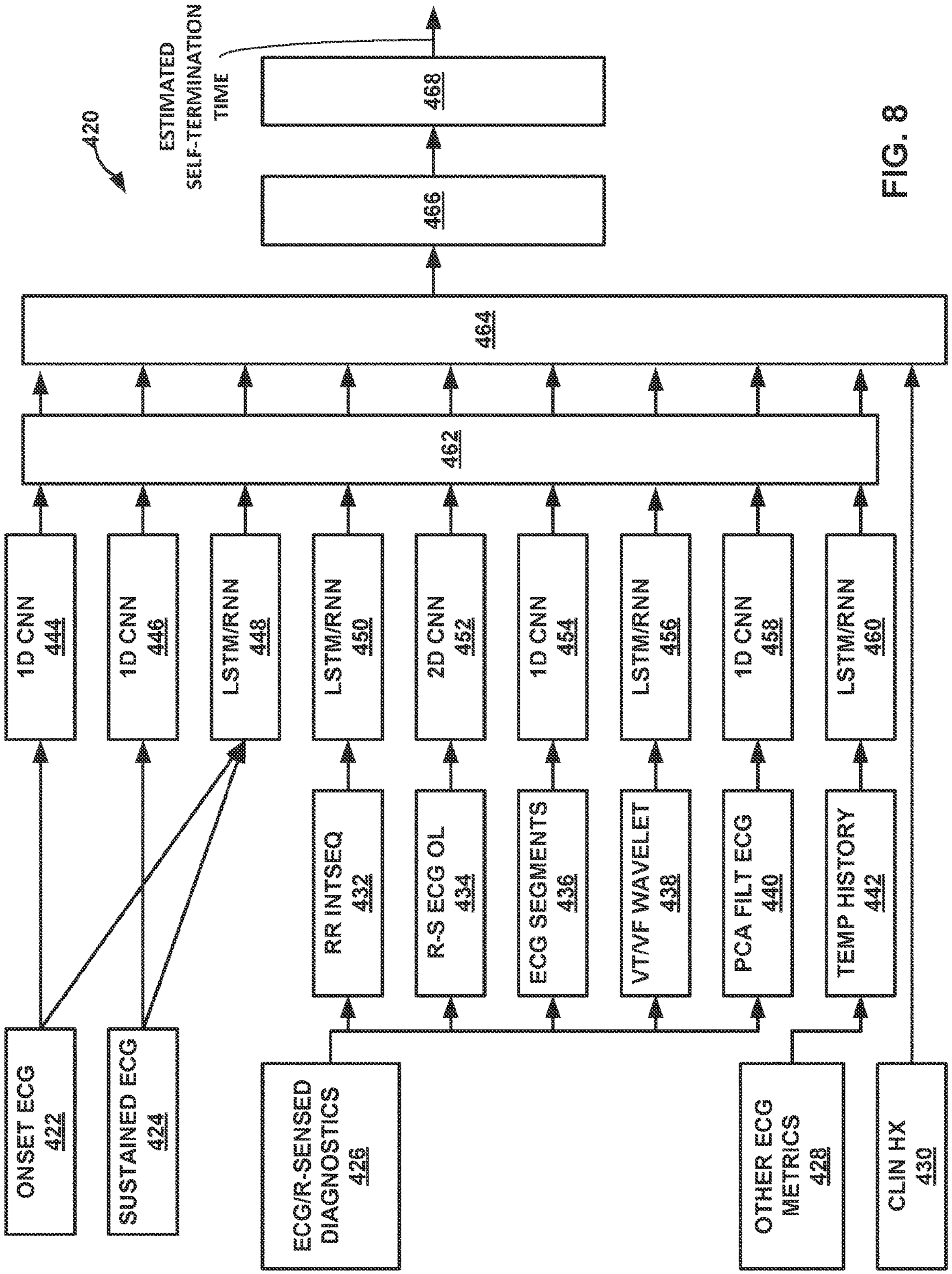
FIG. 8 is a block diagram illustrating an example of an ensemble network for prediction of self-termination time according to one or more aspects of this disclosure.

FIG. 8 is a block diagram illustrating an example of an ensemble network for prediction of self-termination time according to one or more aspects of this disclosure. In some examples, each input (e.g., onset ECG, sustained ECG, ECG, R-sense, short term heart rate variability before onset, history of self-termination, other sensor data, history of self-termination, clinical history, etc.), or portions thereof, may be fed into separate individual neural networks, the output of which may be concatenated and ensembled together in an ensemble neural network. In some examples, all of the inputs may be combined into an ensemble input and fed into a single network which has both RNN and CNN components. In some examples, some of the inputs, or portions thereof, may be fed into separate individual neural networks, while other of the inputs may be combined into a first ensemble network. In such examples, the output of each may be concatenated and ensembled together in a second ensemble neural network, which may be the same as the first ensemble neural network or different than the first ensemble neural network. In some examples, processing circuitry 50 of IMD 10 may analyze such data, such as compare such data, and predict which VT or VF will self-terminate and which ones will not. In other examples, processing circuitry 130 of computing device(s) 12 or IoT device(s) 30 may analyze such data and predict which VT or VF will self-terminate and which ones will not. In some examples, processing circuitry of HMS 22 may analyze (e.g., compare) such data and predict which VT or VF will self-terminate and which ones will not. In some examples, processing circuitry of any combination of devices of system 2 may analyze such data and predict which VT or VF will self-terminate and which ones will not.

For example, processing circuitry of system 2 may analyze historical sensed physiological data of patient 4, history of self-termination status of cardiac events, and/or historical information regarding patient 4 to train a machine learning model. Processing circuitry of system 2 may, upon determining that a VT or VF event is occurring to patient 4, analyze current sensed physiological data of patient 4 using such a machine learning model. In some examples, processing circuitry of system 2, using the machine learning model, may generate a score or a probability that the current VT or VF event will or will not self-terminate within a predetermined amount of time, for example in the range of 30 seconds to 5 minutes. In some examples, the predetermined amount of time may be different for different types of cardiac episodes. For example, for a PVT, the predetermined amount of time may be 30 seconds, while for an MVT, the predetermined amount of time may be 5 minutes. In some examples, the predetermined period of time may by on the order of 2 minutes (e.g., before any serious effects may occur, before a therapy would be able to be delivered, or before EMS would be able to arrive in response to an issued alert). Processing circuitry of system 2 may compare that score or probability to a threshold. In response to the comparison, processing circuitry of system 2 may determine or predict whether the current VT or VF will self-terminate or whether the current VT or VF will not self-terminate.

For example, if processing circuitry of system 2 predicts that the current VT or VF will not self-terminate, processing circuitry of system 2 may initiate a shock, send an alert, or dispatch drone 46 or robot 48, to verify the cardiac event or provide treatment. If processing circuitry of system 2 predicts that the current VT or VF will self-terminate, processing circuitry of system 2 may refrain from initiating a shock, sending an alert, or activating drone 46 or robot 48. As such, system 2 may only provide treatment or send an alert seeking treatment when such treatment may be necessary, thereby reducing the times that unnecessary treatment is provided and saving resources, such as EMS resources.

Ensemble network 420 may operate as follows. For example, processing circuitry of system 2 may feed onset ECG 422, e.g., captured by IMD 10, to 1D CNN 444 and/or LSTM/RNN 448. Onset ECG 422 may include ECG segment(s) during the onset of the cardiac event. Processing circuitry of system 2 may feed sustained ECG 424 to 1D CNN 446 and/or LSTM/RNN 448. Sustained ECG 424 may include ECG segment(s) prior to, during, and/or after the onset of the cardiac event. Sustained ECG 424 may typically be of a longer duration than onset ECG 422.

Processing circuitry of system 2 may feed ECG and/or R-sensed diagnostics 426, to ensemble network 420 as well. For example, processing circuitry of system 2 may feed RR interval sequences from, e.g., a flashback memory, (RR INT SEQ 432) to LSTM/RNN 450. For example, the flashback memory may record trial and ventricular intervals that occur immediately prior to tachyarrhythmia episodes or the most recent interrogation of IMD 10. Processing circuitry of system 2 may feed an R-sense-based ECG overlay (which may include, e.g., time correlated R-sense markers and a digitized ECG) (R-S ECG OL 434) to 2D CNN 452. Processing circuitry of system 2 may feed auto-correlated (Acorr) and/or cross-correlated (Xcorr) ECG segments (ECG Segments 436) to 1D CNN 454. Processing circuitry of system 2 may feed VT/VF-based wavelet scattering (VTNF Wavelet 438) to LSTM/RNN 456. Processing circuitry of system 2 may feed VT/VF principal component analysis (PCA)-based filtering of ECG (PCA FILT ECG 440) to 1D CNN 458.

Processing circuitry of system 2 may feed other or additional ECG metrics which may include a temporal history (Temp History 442) to LSTM/RNN 460. Such other ECG metrics may include a short term heart rate variability (HRV) before onset, history of self termination, other sensor derived diagnostics (e.g., from IMD 10), or the like.

Processing circuitry of system 2 may feed clinical history (Clin Hx 430), for example, from, e.g., EHR data 194, to concatenator 464. Elements 444-460 of ensemble network 420 may process input data and output processed input data to flattener 462. Flattener 462 may reshape the processed input data to generate reshaped processed data. Flattener 462 may output the reshaped processed data to concatenator 464. Concatenator 464 may concatenate the reshaped processed data with the clinical history. Concatenator 464 may output concatenated data to fully connected layer 466. Fully connected layer 466 may output data to regression layer 468 which may estimate a self-termination time for the current cardiac event and output the estimated self-termination time.

Figure 9:
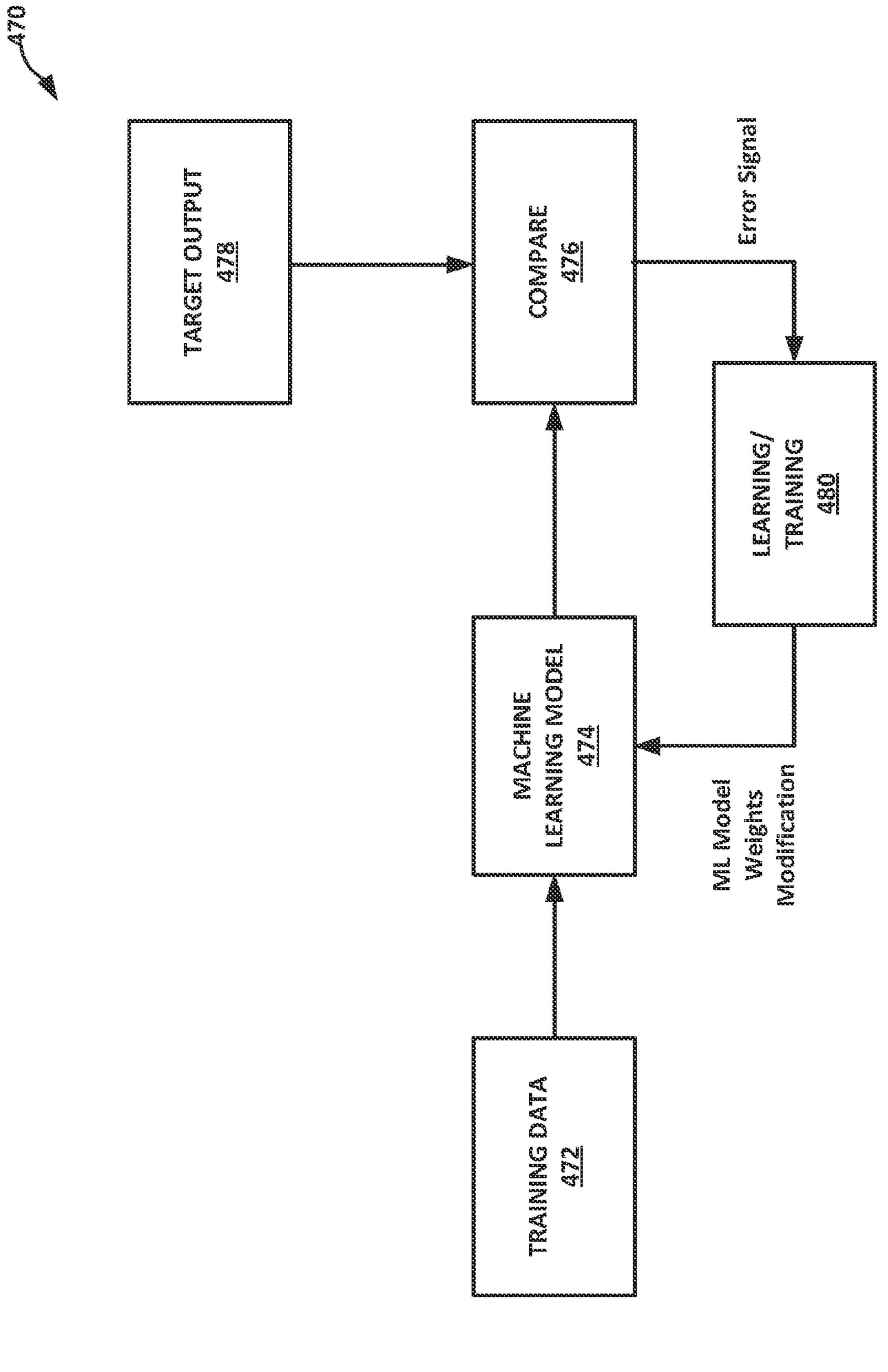
FIG. 9 is a conceptual diagram illustrating an example training process for a machine learning model according to one or more aspects of this disclosure.

FIG. 9 is a conceptual diagram illustrating an example training process for a machine learning or artificial intelligence model according to one or more aspects of this disclosure. Process 470 may be used to train classifier 410 and/or self-termination predictor 412 (both of FIG. 7) and/or ensemble network 420 (FIG. 8). A machine learning (or artificial intelligence) model 474 may be implemented using any number of models for supervised and/or reinforcement learning, such as but not limited to, an artificial neural network, a decision tree, naïve Bayes network, support vector machine, or k-nearest neighbor model, CNN, RNN, LSTM, ensemble network, to name only a few examples. In some examples, one or more of IMD 10, external device(s) 12, IoT device(s) 30, computing system(s) 20, or HMS 22 initially trains machine learning model 474 based on a corpus of training data 472. Training data 474 may include, for example, historical sensed physiological data of patient 4, history of self-termination status of cardiac events, historical information regarding patient 4, other training data discussed herein, and/or the like.

While training machine learning model 474 (which may include classifier 410, self-termination predictor 412, and/or element(s) of or all of ensemble network 420), processing circuitry of system 2 may compare 476 a prediction or classification by classifier 410, self-termination predictor 412, and/or ensemble network 420 (or any element(s) thereof) with a target output 478. Processing circuitry of system 2 utilize an error signal from the comparison to train (learning/training 480) machine learning model 474. Processing circuitry of system 2 may generate machine learning model weights or other modifications which processing circuitry of system 2 may use to modify machine learning model 474. For examples, processing circuitry of system 2 may modify classifier 410, self-termination predictor 412, and/or ensemble network 420 (or any element(s) thereof)

based on the learning/training 480. For example, one or more of IMD 10, external device(s) 12, IoT device(s) 30, computing system(s) 20, or HMS 22, may, for each training instance in training data 472, modify, based on training data 472, classifier 410, self-termination predictor 412, and/or ensemble network 420 (or any element(s) thereof), the manner in which an estimated self-termination time is determined.

Figure 10:
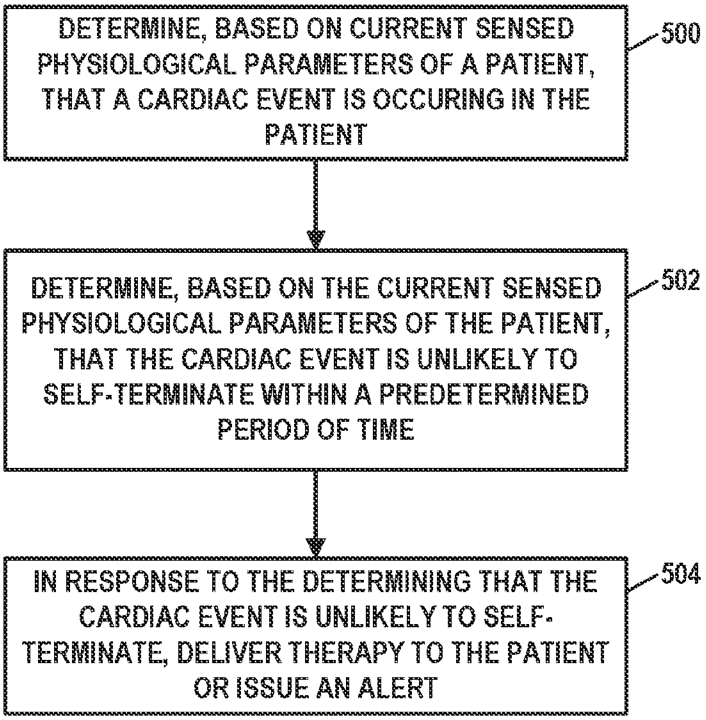
FIG. 10 is a flow diagram illustrating techniques regarding cardiac events that are unlikely to self-terminate according to one or more aspects of this disclosure.

FIG. 10 is a flow diagram illustrating techniques regarding cardiac events that are unlikely to self-terminate according to one or more aspects of this disclosure. While described herein as being performed by processing circuitry of system 2, these techniques may be performed by any one of or any combination of devices of system 2. Processing circuitry of system 2 may determine, based on current sensed physiological parameters of patient 4, that a cardiac event is occurring in patient 4 (500). For example, processing circuitry of any of IMD 10, external devices 12, and/or IoT devices 30 may monitor physiological parameters of patient 4, through various sensor signal(s), such as an ECG signal and may determine that a cardiac event is occurring based on such signals.

Processing circuitry of system 2 may determine, based at least in part on the current sensed physiological parameters of the patient, that the cardiac event is unlikely to self-terminate within a predetermined period of time (502). For example, processing circuitry of any of IMD 10, external devices 12, IoT devices 30, drone 46, robot 48, and/or HMS 22 may employ a machine learning model to determine that the cardiac event is unlikely to self-terminate. The machine learning model may be trained on at least one of historical sensed physiological parameters, history of self-termination status of cardiac events, or historical information about patient 4. In some examples, processing circuitry of system 2 may train the machine learning model. In some examples, the historical sensed physiological parameters and/or the history of self-termination status of cardiac events are specific to patient 4. In other examples, at least one of the historical sensed physiological parameters and/or at least one of the cardiac events of the history of self-termination status of cardiac events are not specific to patient 4 (e.g., the at least one of the historical sensed physiological parameters was sensed in another patient and/or at least one of the cardiac events in the history of self-termination status of cardiac events was historical information for another patient). In some examples, the historical sensed physiological parameters include at least one of electrocardiogram morphologies, bio markers, activity level, posture, or heart rate variability data. In some examples, the historical information about the patient includes at least one of prior heart rhythms or demographical data. In some examples, to determine that the cardiac event is unlikely to self-terminate within the predetermined period of time, processing circuitry of system 2 may compare the current sensed physiological parameters to the historical sensed physiological parameters, determine a score based on the comparison, and compare that score to a predetermined threshold, wherein the predetermined threshold is indicative of a likelihood that the cardiac event will self-terminate.

Processing circuitry of system 2 may, in response to the comparison indicating that the cardiac event is unlikely to self-terminate, deliver therapy to patient 4 or issue an alert (504). For example, processing circuitry of any of IMD 10, external devices 12, IoT devices 30, drone 46, robot 48, and/or HMS 22 may, upon determining that the cardiac event is unlikely to self-terminate, deliver a shock to patient 4, issue an alert to bystander 26, drone 46, robot 48, and/or an EMS. The alert may include the current physiological parameters of patient 4, a location of patient 4 (e.g., as determined by GPS data of computing devices 12, data from IoT devices 30, date from drone 46, or data from robot 48), the determined likelihood that the cardiac event will self-terminate, etc. Such an alert may also include visual or audible indications to draw the attention of bystander 26, such as flashing lights of any of IoT devices 30 or audible alarms of any of IoT devices 30, information for treating patient 4, instructions on how to use AED 44, or the like. If the alert is issued to drone 46 or robot 48, that alert may dispatch drone 46 or robot 48 to treat patient 4 or verify that treatment is needed.

In some examples, determining that the cardiac event is unlikely to self-terminate is further based on at least one of historical sensed physiological parameters, history of self-termination status of cardiac events, or historical information about the patient. In some examples, determining that the cardiac event is unlikely to self-terminate is biased towards determining that the cardiac event is unlikely to self-terminate. For example, the determination that the cardiac event is unlikely to self-terminate may be a determination that the likelihood that the cardiac event will self-terminate is 60%, 70%, or some other number higher than 50%, but less than 100%, rather than 50%.

In some examples, the cardiac event is a ventricular tachycardia or a ventricular fibrillation.

In some examples, the current sensed physiological parameters are first current sensed physiological parameters, the cardiac event is a first cardiac event, the score is a first score, and the alert is a first alert. In such examples, processing circuitry of system 2, may determine, based on second current sensed physiological parameters of patient 4, that a second cardiac event is occurring in patient 4. Processing circuitry of system 2 may determine, based on the second current sensed physiological parameters of the patient, that the second cardiac event is likely to self-terminate within the predetermined period of time. In response to determining that the second cardiac event is likely to self-terminate within the predetermined period of time, refrain from delivering therapy to the patient or issuing a second alert.

Figure 11A:
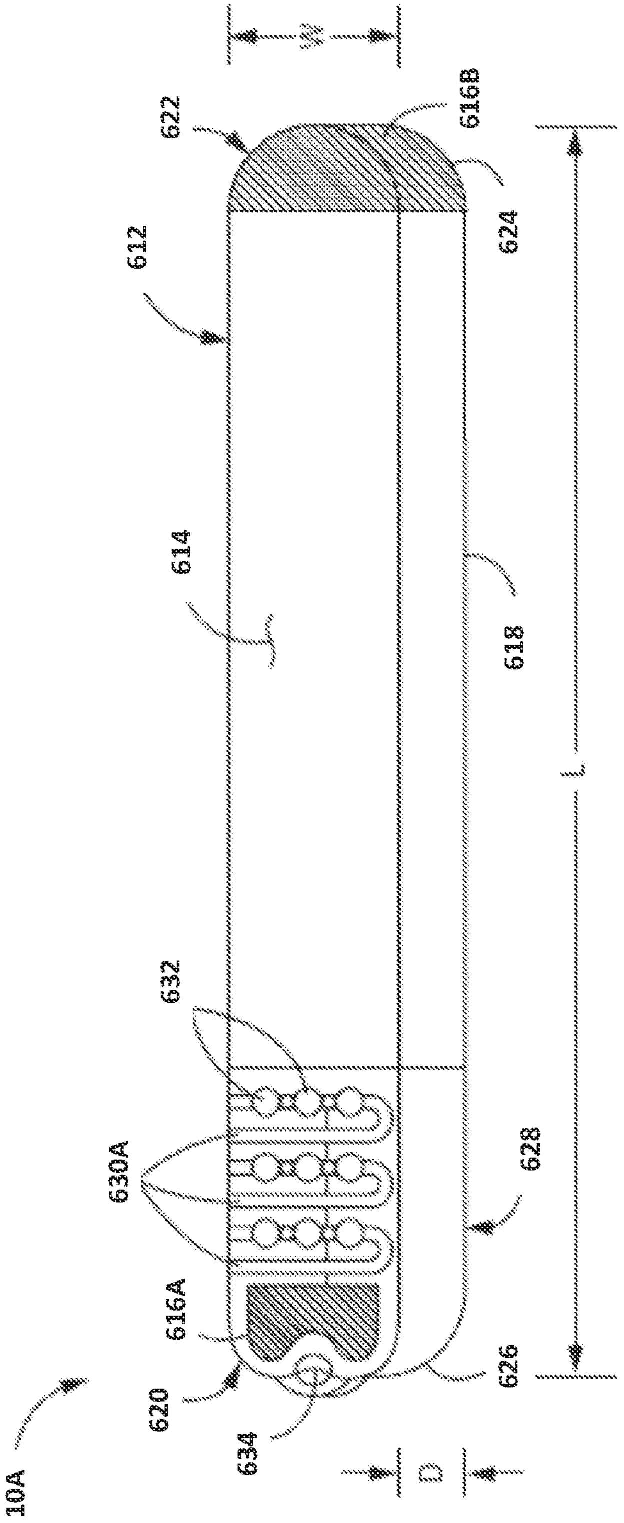
FIG. 11A is a perspective drawing illustrating an insertable cardiac monitor.

FIG. 11A is a perspective drawing illustrating an IMD 10A, which may be an example configuration of IMD 10 of FIGS. 1 and 2 as an ICM. In the example shown in FIG. 11A, IMD 10A may be embodied as a monitoring device having housing 612, proximal electrode 616A and distal electrode 616B. Housing 612 may further comprise first major surface 614, second major surface 618, proximal end 620, and distal end 622. Housing 612 encloses electronic circuitry located inside the IMD 10A and protects the circuitry contained therein from body fluids. Housing 612 may be hermetically sealed and configured for subcutaneous implantation. Electrical feedthroughs provide electrical connection of electrodes 616A and 616B.

In the example shown in FIG. 11A, IMD 10A is defined by a length L, a width Wand thickness or depth D and is in the form of an elongated rectangular prism wherein the length L is much larger than the width W, which in turn is larger than the depth D. In one example, the geometry of the IMD 10A—in particular a width W greater than the depth D—is selected to allow IMD 10A to be inserted under the skin of the patient using a minimally invasive procedure and to remain in the desired orientation during insertion. For example, the device shown in FIG. 11A includes radial asymmetries (notably, the rectangular shape) along the longitudinal axis that maintains the device in the proper orientation following insertion. For example, the spacing between proximal electrode 616A and distal electrode 616B may range from 5 millimeters (mm) to 55 mm, 30 mm to 55 mm, 35 mm to 55 mm, and from 40 mm to 55 mm and may be any range or individual spacing from 5 mm to 60 mm. In addition, IMD 10A may have a length L that ranges from 30 mm to about 70 mm. In other examples, the length L may range from 5 mm to 60 mm, 40 mm to 60 mm, 45 mm to 60 mm and may be any length or range of lengths between about 30 mm and about 70 mm. In addition, the width W of major surface 614 may range from 3 mm to 15, mm, from 3 mm to 10 mm, or from 5 mm to 15 mm, and may be any single or range of widths between 3 mm and 15 mm. The thickness of depth D of IMD 10A may range from 2 mm to 15 mm, from 2 mm to 9 mm, from 2 mm to 5 mm, from 5 mm to 15 mm, and may be any single or range of depths between 2 mm and 15 mm. In addition, IMD 10A according to an example of the present disclosure is has a geometry and size designed for ease of implant and patient comfort. Examples of IMD 10A described in this disclosure may have a volume of three cubic centimeters (cm) or less, 1.5 cubic cm or less or any volume between three and 1.5 cubic centimeters.

In the example shown in FIG. 11A, once inserted within the patient, the first major surface 614 faces outward, toward the skin of the patient while the second major surface 618 is located opposite the first major surface 614. In addition, in the example shown in FIG. 11A, proximal end 620 and distal end 622 are rounded to reduce discomfort and irritation to surrounding tissue once inserted under the skin of the patient. IMD 10A, including instrument and method for inserting IMD 10 is described, for example, in U.S. Patent Publication No. 2014/0276928, incorporated herein by reference in its entirety.

Proximal electrode 616A is at or proximate to proximal end 620, and distal electrode 616B is at or proximate to distal end 622. Proximal electrode 616A and distal electrode 616B are used to sense cardiac EGM signals, e.g., ECG signals, thoracically outside the ribcage, which may be sub-muscularly or subcutaneously. Cardiac signals may be stored in a memory of IMD 10A, and data may be transmitted via integrated antenna 630A to another device, which may be another implantable device or an external device, such as external device 612. In some example, electrodes 616A and 616B may additionally or alternatively be used for sensing any bio-potential signal of interest, which may be, for example, an EGM, EEG, EMG, or a nerve signal, or for measuring impedance, from any implanted location.

In the example shown in FIG. 11A, proximal electrode 616A is at or in close proximity to the proximal end 620 and distal electrode 616B is at or in close proximity to distal end 622. In this example, distal electrode 616B is not limited to a flattened, outward facing surface, but may extend from first major surface 614 around rounded edges 624 and/or end surface 626 and onto the second major surface 618 so that the electrode 616B has a three-dimensional curved configuration. In some examples, electrode 616B is an uninsulated portion of a metallic, e.g., titanium, part of housing 612.

In the example shown in FIG. 11A, proximal electrode 616A is located on first major surface 614 and is substantially flat, and outward facing. However, in other examples proximal electrode 616A may utilize the three dimensional curved configuration of distal electrode 616B, providing a three dimensional proximal electrode (not shown in this example). Similarly, in other examples distal electrode 616B may utilize a substantially flat, outward facing electrode located on first major surface 614 similar to that shown with respect to proximal electrode 616A.

The various electrode configurations allow for configurations in which proximal electrode 616A and distal electrode 616B are located on both first major surface 614 and second major surface 618. In other configurations, such as that shown in FIG. 11A, only one of proximal electrode 616A and distal electrode 616B is located on both major surfaces 614 and 618, and in still other configurations both proximal electrode 616A and distal electrode 616B are located on one of the first major surface 614 or the second major surface 618 (e.g., proximal electrode 616A located on first major surface 614 while distal electrode 616B is located on second major surface 618). In another example, IMD 10A may include electrodes on both major surface 614 and 618 at or near the proximal and distal ends of the device, such that a total of four electrodes are included on IMD 10A. Electrodes 616A and 616B may be formed of a plurality of different types of biocompatible conductive material, e.g. stainless steel, titanium, platinum, iridium, or alloys thereof, and may utilize one or more coatings such as titanium nitride or fractal titanium nitride.

In the example shown in FIG. 11A, proximal end 620 includes a header assembly 628 that includes one or more of proximal electrode 616A, integrated antenna 630A, anti-migration projections 632, and/or suture hole 634. Integrated antenna 630A is located on the same major surface (i.e., first major surface 614) as proximal electrode 616A and is also included as part of header assembly 628. Integrated antenna 630A allows IMD 10A to transmit and/or receive data. In other examples, integrated antenna 630A may be formed on the opposite major surface as proximal electrode 616A, or may be incorporated within the housing 612 of IMD 10A. In the example shown in FIG. 11A, anti-migration projections 632 are located adjacent to integrated antenna 630A and protrude away from first major surface 614 to prevent longitudinal movement of the device. In the example shown in FIG. 1A, anti-migration projections 632 include a plurality (e.g., nine) small bumps or protrusions extending away from first major surface 614. As discussed above, in other examples anti-migration projections 632 may be located on the opposite major surface as proximal electrode 616A and/or integrated antenna 630A. In addition, in the example shown in FIG. 11A, header assembly 628 includes suture hole 634, which provides another means of securing IMD 10A to the patient to prevent movement following insertion. In the example shown, suture hole 634 is located adjacent to proximal electrode 616A. In one example, header assembly 628 is a molded header assembly made from a polymeric or plastic material, which may be integrated or separable from the main portion of IMD 10A.

Figure 11B:
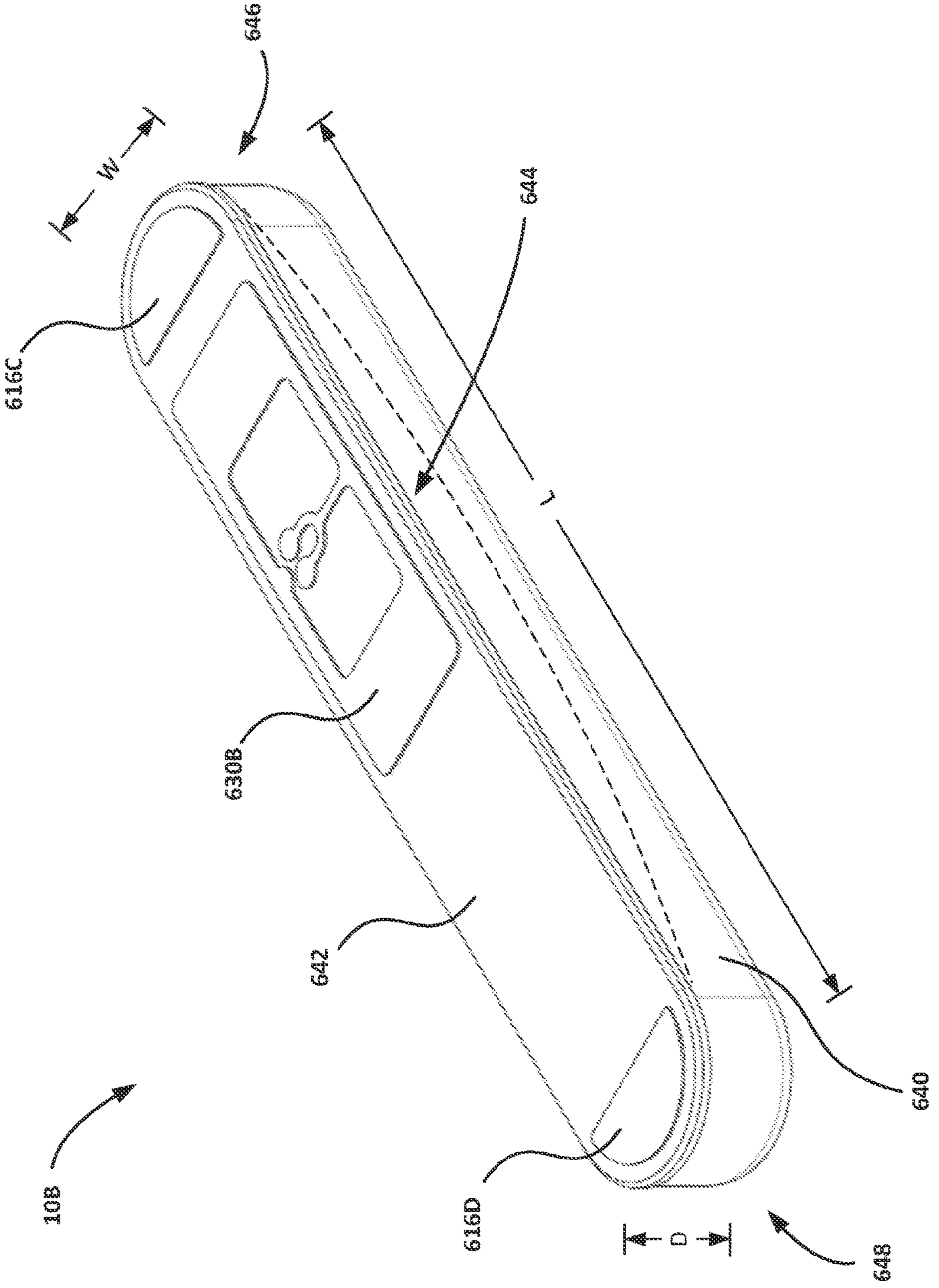
FIG. 11B is a perspective drawing illustrating another insertable cardiac monitor.

FIG. 11B is a perspective drawing illustrating another IMD 10B, which may be another example configuration of IMD 10 from FIGS. 1 and 2 as an ICM. IMD 10B of FIG. 11B may be configured substantially similarly to IMD 10A of FIG. 11A, with differences between them discussed herein.

IMD 10B may include a leadless, subcutaneously-implantable monitoring device, e.g. an ICM. IMD 10B includes housing having a base 640 and an insulative cover 642. Proximal electrode 616C and distal electrode 616D may be formed or placed on an outer surface of cover 642. Various circuitries and components of IMD 10B, e.g., described above with respect to FIG. 2, may be formed or placed on an inner surface of cover 642, or within base 640. In some examples, a battery or other power source of IMD 10B may be included within base 640. In the illustrated example, antenna 630B is formed or placed on the outer surface of cover 642, but may be formed or placed on the inner surface in some examples. In some examples, insulative cover 642 may be positioned over an open base 640 such that base 640 and cover 642 enclose the circuitries and other components and protect them from fluids such as body fluids. The housing including base 640 and insulative cover 642 may be hermetically sealed and configured for subcutaneous implantation.

Circuitries and components may be formed on the inner side of insulative cover 642, such as by using flip-chip technology. Insulative cover 642 may be flipped onto a base 640. When flipped and placed onto base 640, the components of IMD 10B formed on the inner side of insulative cover 642 may be positioned in a gap 644 defined by base 640. Electrodes 616C and 616D and antenna 630B may be electrically connected to circuitry formed on the inner side of insulative cover 642 through one or more vias (not shown) formed through insulative cover 642. Insulative cover 642 may be formed of sapphire (i.e., corundum), glass, parylene, and/or any other suitable insulating material. Base 640 may be formed from titanium or any other suitable material (e.g., a biocompatible material). Electrodes 616C and 616D may be formed from any of stainless steel, titanium, platinum, iridium, or alloys thereof. In addition, electrodes 616C and 616D may be coated with a material such as titanium nitride or fractal titanium nitride, although other suitable materials and coatings for such electrodes may be used.

In the example shown in FIG. 11B, the housing of IMD 10B defines a length L, a width Wand thickness or depth D and is in the form of an elongated rectangular prism wherein the length L is much larger than the width W, which in turn is larger than the depth D, similar to IMD 10A of FIG. 11A. For example, the spacing between proximal electrode 616C and distal electrode 616D may range from 5 mm to 50 mm, from 30 mm to 50 mm, from 35 mm to 45 mm, and may be any single spacing or range of spacings from 5 mm to 50 mm, such as approximately 40 mm. In addition, IMD 10B may have a length L that ranges from 5 mm to about 70 mm. In other examples, the length L may range from 30 mm to 70 mm, 40 mm to 60 mm, 45 mm to 55 mm, and may be any single length or range of lengths from 5 mm to 50 mm, such as approximately 45 mm. In addition, the width W may range from 3 mm to 15 mm, 5 mm to 15 mm, 5 mm to 10 mm, and may be any single width or range of widths from 3 mm to 15 mm, such as approximately 8 mm. The thickness or depth D of IMD 10B may range from 2 mm to 15 mm, from 5 mm to 15 mm, or from 3 mm to 5 mm, and may be any single depth or range of depths between 2 mm and 15 mm, such as approximately 4 mm. IMD 10B may have a volume of three cubic centimeters (cm) or less, or 1.5 cubic cm or less, such as approximately 1.4 cubic cm.

In the example shown in FIG. 11B, once inserted subcutaneously within the patient, outer surface of cover 642 faces outward, toward the skin of the patient. In addition, as shown in FIG. 11B, proximal end 646 and distal end 648 are rounded to reduce discomfort and irritation to surrounding tissue once inserted under the skin of the patient. In addition, edges of IMD 10B may be rounded.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module, unit, or circuit for purposes of clarity, it should be understood that the techniques of this disclosure may be performed by a combination of units, modules, or circuitry associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" or "processing circuitry" as used herein may refer to any of the foregoing structure or any other physical structure suitable for implementation of the described techniques. Also, the techniques could be fully implemented in one or more circuits or logic elements.

This disclosure includes the following non-limiting examples.

Example 1A. A method comprising: determining, by processing circuitry and based on current sensed physiological parameters of a patient, that a cardiac event is occurring in the patient; determining, by the processing circuitry and based on the current sensed physiological parameters of the patient, that the cardiac event is unlikely to self-terminate within a predetermined period of time; and in response to determining that the cardiac event is unlikely to self-terminate, deliver therapy to the patient or issue an alert.

Example 2A. The method of example 1A, wherein determining that the cardiac event is unlikely to self-terminate is further based on at least one of historical sensed physiological parameters, history of self-termination status of cardiac events, or historical information about the patient.

Example 3A. The method of example 2A, wherein the historical sensed physiological parameters comprise at least one of electrocardiogram morphologies, bio markers, activity level, posture, or heart rate variability data.

Example 4A. The method of example 2A or example 3A, wherein the historical information about the patient comprises at least one of prior heart rhythms or demographic data.

Example 5A. The method of any one of more of examples 1A-4A, wherein the processing circuitry employs a machine learning algorithm to determine that the cardiac event is unlikely to self-terminate within the predetermined period of time.

Example 6A. The method of example 5A, wherein the machine learning algorithm is trained on at least one of historical sensed physiological parameters, history of self-termination status of cardiac events, or historical information about the patient.

Example 7A. The method of example 6A, further comprising training the machine learning algorithm.

Example 8A. The method of any one or more of examples 1A-7A, wherein determining that the cardiac event is unlikely to self-terminate comprises: comparing the current sensed physiological parameters to historical sensed physiological parameters; determining a score based on the comparison; and comparing the score to a predetermined threshold, wherein the predetermined threshold is indicative of a likelihood that the cardiac event will self-terminate.

Example 9A. The method of any one or more of examples 1A-8A, wherein determining that the cardiac event is unlikely to self-terminate is biased towards determining that the cardiac event is unlikely to self-terminate.

Example 10A. The method of any one or more of examples 1A-9A, wherein the cardiac event is a ventricular tachycardia or a ventricular fibrillation.

Example 11A. The method of any one or more of examples 1A-10A, wherein the current sensed physiological parameters are first current sensed physiological parameters, the cardiac event is a first cardiac event, the score is a first score, and the alert is a first alert, the method further comprising: determining, by the processing circuitry and based on second current sensed physiological parameters of a patient, that a second cardiac event is occurring in the patient; determining, by the processing circuitry and based on the second current sensed physiological parameters of the patient, that the second cardiac event is likely to self-terminate within the predetermined period of time; and in response to determining that the second cardiac event is likely to self-terminate within the predetermined period of time, refrain from delivering therapy to the patient or issuing an alert.

Example 12A. A medical device system configured to implement any one or more of examples 1A-11A.

Example 13A. A non-transitory computer-readable medium, storing instructions, which when executed, cause processing circuitry of a medical device system to perform the method of any one or more of examples 1A-11A.

Example 14A. A medical device system comprising: communication circuitry configured to communicate with a medical device system; memory communicatively coupled to the communication circuitry and being configured to store current sensed physiological parameters of a patient; and processing circuitry communicatively coupled to the communication circuitry and the memory, the processing circuitry being configured to: determine, based on the current sensed physiological parameters of the patient, that a cardiac event is occurring in the patient: determine, based on the current sensed physiological parameters of the patient, that the cardiac event is unlikely to self-terminate within a predetermined period of time; and deliver, in response to determining that the cardiac event is unlikely to self-terminate, therapy to the patient or issue an alert.

Example 15A. The system of example 14A, wherein the processing circuitry is configured to determine that the cardiac event is unlikely to self-terminate further based on at least one of historical sensed physiological parameters, history of self-termination status of cardiac events, or historical information about the patient.

Example 16A. The system of example 15A, wherein the historical sensed physiological parameters comprise at least one of electrocardiogram morphologies, bio markers, activity level, posture, or heart rate variability data.

Example 17A. The system of example 15A or example 16A, wherein the historical information about the patient comprises at least one of prior heart rhythms or demographic data.

Example 18A. The system of any one of more of examples 14A-17A, wherein the processing circuitry employs a machine learning algorithm to determine that the cardiac event is unlikely to self-terminate within the predetermined period of time.

Example 19A. The system of example 18A, wherein the machine learning algorithm is trained on at least one of historical sensed physiological parameters, history of self-termination status of cardiac events, or historical information about the patient.

Example 20A. The system of example 19A, wherein the processing circuitry is further configured to train the machine learning algorithm.

Example 21A. The system of any one or more of examples 14A-20A, wherein as part of determining that the cardiac event is unlikely to self-terminate, the processing circuitry is configured to: compare the current sensed physiological parameters to historical sensed physiological parameters; determine a score based on the comparison; and compare the score to a predetermined threshold, wherein the predetermined threshold is indicative of a likelihood that the cardiac event will self-terminate.

Example 22A. The system of any one or more of examples 14A-21A, wherein determining that the cardiac event is unlikely to self-terminate is biased towards determining that the cardiac event is unlikely to self-terminate.

Example 23A. The system of any one or more of examples 14A-22A, wherein the cardiac event is a ventricular tachycardia or a ventricular fibrillation.

Example 24A. The system of any one or more of examples 14A-23A, wherein the current sensed physiological parameters are first current sensed physiological parameters, the cardiac event is a first cardiac event, the score is a first score, and the alert is a first alert, the processing circuitry being further configured to: determine, based on second current sensed physiological parameters of a patient, that a second cardiac event is occurring in the patient; determine, based on the second current sensed physiological parameters of the patient, that the second cardiac event is likely to self-terminate within the predetermined period of time; and refrain from, in response to determining that the second cardiac event is likely to self-terminate within the predetermined period of time, delivering therapy to the patient or issuing an alert.

Example 1B. A medical device system comprising: an implantable medical device (IMD) configured to sense physiological parameters of a patient; memory configured to store current sensed physiological parameters of the patient; and processing circuitry communicatively coupled to the memory, the processing circuitry being configured to: determine, based on the current sensed physiological parameters of the patient, that a cardiac event is occurring in the patient; determine, based on the current sensed physiological parameters of the patient, that the cardiac event is unlikely to self-terminate within a predetermined period of time; and in response to determining that the cardiac event is unlikely to self-terminate, control delivery of therapy to the patient or issue an alert.

Example 2B. The system of example 1B, wherein the processing circuitry is configured to determine that the cardiac event is unlikely to self-terminate further based on at least one of historical sensed physiological parameters, history of self-termination status of cardiac events, or historical information about the patient.

Example 3B. The system of example 2B, wherein the historical sensed physiological parameters comprise at least one of electrocardiogram morphologies, bio markers, activity level, posture, or heart rate variability data.

Example 4B. The system of example 2B or example 3B, wherein the historical information about the patient comprises at least one of prior heart rhythms or demographic data.

Example 5B. The system of any one of more of examples 1B-4B, wherein the processing circuitry employs a machine learning model to determine that the cardiac event is unlikely to self-terminate within the predetermined period of time.

Example 6B. The system of example 5B, wherein the machine learning model is trained on at least one of historical sensed physiological parameters, history of self-termination status of cardiac events, or historical information about the patient.

Example 7B. The system of example 6B, wherein the processing circuitry is further configured to train the machine learning model.

Example 8B. The system of any one or more of examples 1B-7B, wherein as part of determining that the cardiac event is unlikely to self-terminate, the processing circuitry is configured to: compare the current sensed physiological parameters to historical sensed physiological parameters; determine a score based on the comparison; and compare the score to a predetermined threshold, wherein the predetermined threshold is indicative of a likelihood that the cardiac event will self-terminate.

Example 9B. The system of any one or more of examples 1B-8B, wherein determining that the cardiac event is unlikely to self-terminate is biased towards determining that the cardiac event is unlikely to self-terminate.

Example 10B. The system of any one or more of examples 1B-9B, wherein the cardiac event is a ventricular tachycardia or a ventricular fibrillation.

Example 11B. The system of any one or more of examples 1B-10B, wherein the current sensed physiological parameters are first current sensed physiological parameters, the cardiac event is a first cardiac event, the score is a first score, and the alert is a first alert, the processing circuitry being further configured to: determine, based on second current sensed physiological parameters of a patient, that a second cardiac event is occurring in the patient; determine, based on the second current sensed physiological parameters of the patient, that the second cardiac event is likely to self-terminate within the predetermined period of time; and refrain from, in response to determining that the second cardiac event is likely to self-terminate within the predetermined period of time, delivering therapy to the patient or issuing an alert.

Various examples have been described. These and other examples are within the scope of the following claims.

What is claimed is:

1. A medical device system comprising:

an implantable medical device (IMD) configured to sense physiological parameters of a patient;

memory configured to store current sensed physiological parameters of the patient; and processing circuitry communicatively coupled to the memory, the processing circuitry being configured to:

determine, based on the current sensed physiological parameters of the patient, that a cardiac event is occurring in the patient;

execute a machine learning model to determine, based on the current sensed physiological parameters of the patient, that the cardiac event is unlikely to self-terminate within a predetermined period of time; and in response to determining that the cardiac event is unlikely to self-terminate, control delivery of therapy to the patient or issue an alert.

2. The system of claim 1, wherein the processing circuitry is configured to determine that the cardiac event is unlikely to self-terminate further based on at least one of historical sensed physiological parameters, history of self-termination status of cardiac events, or historical information about the patient.

3. The system of claim 2, wherein the historical sensed physiological parameters comprise at least one of electrocardiogram morphologies, bio markers, activity level, posture, or heart rate variability data.

4. The system of claim 2, wherein the historical information about the patient comprises at least one of prior heart rhythms or demographic data.

5. The system of claim 1, wherein the machine learning model is trained on at least one of historical sensed physiological parameters, history of self-termination status of cardiac events, or historical information about the patient.

6. The system of claim 5, wherein the processing circuitry is further configured to train the machine learning model.

7. The system of claim 1, wherein as part of determining that the cardiac event is unlikely to self-terminate, the processing circuitry is configured to:

compare the current sensed physiological parameters to historical sensed physiological parameters;

determine a score based on the comparison; and compare the score to a predetermined threshold, wherein the predetermined threshold is indicative of a likelihood that the cardiac event will self-terminate.

8. The system of claim 1, wherein determining that the cardiac event is unlikely to self-terminate is biased towards determining that the cardiac event is unlikely to self-terminate.

9. The system of claim 1, wherein the cardiac event is a ventricular tachycardia or a ventricular fibrillation.

10. The system of claim 1, wherein the current sensed physiological parameters are first current sensed physiological parameters, the cardiac event is a first cardiac event, the therapy is a first therapy, and the alert is a first alert, the processing circuitry being further configured to:

determine, based on second current sensed physiological parameters of a patient, that a second cardiac event is occurring in the patient;

determine, based on the second current sensed physiological parameters of the patient, that the second cardiac event is likely to self-terminate within the predetermined period of time; and refrain from, in response to determining that the second cardiac event is likely to self-terminate within the predetermined period of time, delivering second therapy to the patient or issuing a second alert.

11. A method comprising:

determining, by processing circuitry and based on current sensed physiological parameters of a patient, that a cardiac event is occurring in the patient;

executing, by the processing circuitry, a machine learning model to determine, based on the current sensed physiological parameters of the patient, that the cardiac event is unlikely to self-terminate within a predetermined period of time; and in response to determining that the cardiac event is unlikely to self-terminate, deliver therapy to the patient or issue an alert.

12. The method of claim 11, wherein determining that the cardiac event is unlikely to self-terminate is further based on at least one of historical sensed physiological parameters, history of self-termination status of cardiac events, or historical information about the patient.

13. The method of claim 12, wherein the historical sensed physiological parameters comprise at least one of electrocardiogram morphologies, bio markers, activity level, posture, or heart rate variability data.

14. The method of claim 12, wherein the historical information about the patient comprises at least one of prior heart rhythms or demographic data.

15. The method of claim 5, wherein the machine learning model is trained on at least one of historical sensed physiological parameters, history of self-termination status of cardiac events, or historical information about the patient.

16. The method of claim 15, further comprising training the machine learning model.

17. The method of claim 11, wherein determining that the cardiac event is unlikely to self-terminate comprises:

comparing the current sensed physiological parameters to historical sensed physiological parameters;

determining a score based on the comparison; and comparing the score to a predetermined threshold, wherein the predetermined threshold is indicative of a likelihood that the cardiac event will self-terminate.

18. Non-transitory computer-readable media, storing instructions, which when executed, cause processing circuitry of a medical device system to:

determine, based on current sensed physiological parameters of a patient, that a cardiac event is occurring in the patient;

execute a machine learning model to determine, based on the current sensed physiological parameters of the patient, that the cardiac event is unlikely to self-terminate within a predetermined period of time; and in response to determining that the cardiac event is unlikely to self-terminate, control delivery of therapy to the patient or issue an alert.

* * * * *